United States Patent [19]

Preston et al.

[11] Patent Number: 4,528,282
[45] Date of Patent: Jul. 9, 1985

[54] AMIDE DERIVATIVES

[75] Inventors: John Preston, Knutsford; William R. Carling, Macclesfield, both of England

[73] Assignee: Imperial Chemical Industries, plc, England

[21] Appl. No.: 459,143

[22] Filed: Jan. 19, 1983

[30] Foreign Application Priority Data

Jan. 22, 1982 [GB] United Kingdom ............... 8201832

[51] Int. Cl.³ .................... A61K 37/00; C07C 103/52
[52] U.S. Cl. ............................... 514/19; 260/112.5 R
[58] Field of Search ............... 260/112.5 R; 424/177; 514/19

[56] References Cited

U.S. PATENT DOCUMENTS

| | | | |
|---|---|---|---|
| 4,296,110 | 10/1981 | Johnson | 424/274 |
| 4,303,583 | 12/1981 | Kim et al. | 424/200 |
| 4,344,949 | 8/1982 | Hoefle et al. | 424/258 |
| 4,350,633 | 9/1982 | Kim | 260/326.11 R |
| 4,350,704 | 9/1982 | Hoefle | 424/274 |
| 4,370,494 | 1/1983 | Wright | 562/450 |
| 4,374,246 | 2/1983 | Wright | 546/156 |
| 4,374,829 | 2/1983 | Harris et al. | 260/112.5 R |
| 4,385,051 | 5/1983 | Oka et al. | 424/177 |
| 4,390,700 | 6/1983 | Stanton | 546/165 |
| 4,397,857 | 8/1983 | Vincent | 424/263 |
| 4,402,969 | 9/1983 | Greenlee | 424/274 |
| 4,410,520 | 10/1983 | Watthey | 424/244 |
| 4,425,355 | 1/1984 | Hoefle | 424/274 |

FOREIGN PATENT DOCUMENTS 2502614 1/1982 United Kingdom ......... 260/112.5 R

Primary Examiner—Delbert R. Phillips
Attorney, Agent, or Firm—Cushman, Darby and Cushman

[57] ABSTRACT

Amide derivatives of the formula:

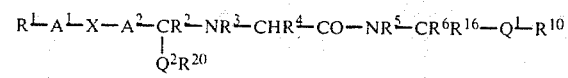

wherein either $R^1$ is aryl or heterocyclic and $A^1$ is a direct link, or $R^1$ is aryl or heterocyclic, or hydrogen, or halogeno, hydroxy, amino, guanidino, mercapto, carboxy, carbamoyl, or a substituted derivative thereof, and $A^1$ is alkylene, alkenylene, cycloalkylene or cycloalkenylene; wherein X is carbonyl or hydroxymethylene or substituted derivatives thereof; wherein $A^2$ is alkylene, alkenylene or alkylidene; wherein $R^2$ is hydrogen or alkyl which is unsubstituted or which bears an aryl substituent, or $R^2$ has the formula $-Q^2-R^{20}$ as defined below; wherein $R^3$ is hydrogen, alkyl or a carbonyl-containing group; wherein $R^4$ is hydrogen or alkyl which is unsubstituted or which bears a halogeno, hydroxy, amino, guanidino, carboxy, carbamoyl, mercapto, alkoxy, alkylamino, dialkylamino, cyclic amino, alkylthio, alkanoylamino, alkoxycarbonylamino, alkoxycarbonyl, alkoxycarbonyl, aryl or heterocyclyl substituent;

wherein $-NR^5-CR^6R^{16}-Q^1-R^{10}$ is an amino acid residue, $R^5$, $R^6$ and $R^{16}$ being defined in claim 1, wherein $Q^1$ and $Q^2$, which may be the same or different, each is carbonyl (—CO—) or methylene (—CH$_2$—); and wherein $R^{10}$ and $R^{20}$, which may be the same or different, is hydroxy, amino or a substituted derivative thereof or hydroxyamino or arylthio; or a salt thereof where appropriate; processes for their manufacture and pharmaceutical compositions containing them. The compounds are inhibitors of angiotensin converting enzyme and may be used in the treatment of hypertension.

13 Claims, No Drawings

AMIDE DERIVATIVES

This invention relates to new amide derivatives and more particularly it relates to amide derivatives which are inhibitors or angiotensin converting enzyme (ACE).

European Patent Specification No. 12401 describes ACE inhibitors of the general formula:

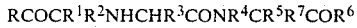

$$RCOCR^1R^2NHCHR^3CONR^4CR^5R^7COR^6$$

wherein the various R groups are defined in said specification. One compound which is described therein is at an advanced stage of clinical trial. This compound is known as MK 421 and has the chemical structure:

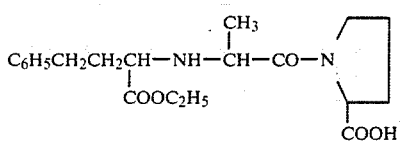

Insofar as European Specification No. 12401 is prior art in respect of the present invention, the critical substituent is $R^1$ as defined in Specification No. 12401. This substituent is 2-phenylethyl in MK421, and is defined in Specification No. 12401 as, inter alia, alkyl bearing one substituent which may be aryl or heteroaryl, or bearing two substituents one of which is aryl or heteroaryl and the other of which is amino or acylamino. There is no disclosure in Specification No. 12401 of any compound wherein the substituent $R^1$ is alkyl bearing an oxo substituent (or a derivative thereof) or bearing an aryl or heteroaryl substituent and a hydroxy substituent.

According to the present invention there is provided an amide derivative of the formula:

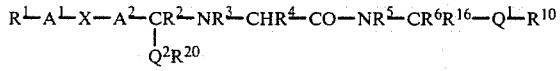

wherein either $R^1$ is aryl or heterocyclic and $A^1$ is a direct link, or $R^1$ is aryl or heterocyclic, or hydrogen, or halogeno, hydroxy, amino, guanidino, mercapto, carboxy, carbamoyl, or $R^1$ has the formula $R^{11}$—O—, $R^{11}R^{21}$N—, $R^{11}R^{21}$N—CO—, $R^{11}$CONH—, $R^{11}$—S— or $R^{11}$—OCO— wherein $R^{11}$ is alkyl of up to 5 carbon atoms or phenyl, and $R^{21}$ is hydrogen or alkyl of up to 5 carbon atoms, and $A^1$ is alkylene of 1 to 15 carbon atoms, alkenylene of 2 to 15 carbon atoms or cycloalkylene or cycloalkenylene each of 3 to 15 carbon atoms; wherein either X has the formula:

—CO—

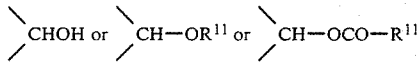

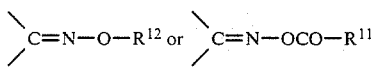

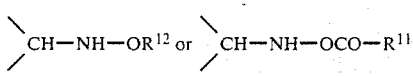

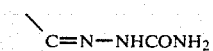

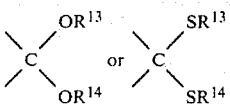

wherein $R^{11}$ has the meaning stated above, wherein $R^{12}$ is hydrogen or alkyl of up to 5 carbon atoms which is unsubstituted or which bears an aryl substituent, and wherein $R^{13}$ and $R^{14}$, which may be the same or different, each is alkyl of up to 5 carbon atoms, or $R^{13}$ and $R^{14}$ are joined together to form alkylene of 2 to 5 carbon atoms, and $A^2$ is alkylene, alkenylene or alkylidene each of up to 5 carbon atoms; or —X—$A^2$— has the formula:

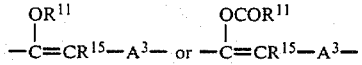

wherein $R^{11}$ has the meaning stated above, and wherein $R^{15}$ is hydrogen or alkyl of up to 3 carbon atoms and $A^3$ is alkylene of 0 to 4 carbon atoms;

wherein $R^2$ is hydrogen or alkyl of up to 5 carbon atoms which is unsubstituted or which bears an aryl substituent, or $R^2$ has the formula —$Q^2$—$R^{20}$ as defined below;

wherein $R^3$ is hydrogen, alkyl of up to 5 carbon atoms or has the formula —$CH_2OCOR^{11}$, —$COR^{21}$ or —$COOR^{11}$ wherein $R^{11}$ and $R^{21}$ have the meanings stated above;

wherein $R^4$ is hydrogen or alkyl of up to 5 carbon atoms which is unsubstituted or which bears a halogeno, hydroxy, amino, guanidino, carboxy, carbamoyl or mercapto substituent, or an alkoxy, alkylamino, dialkylamino, cyclic amino or alkylthio substituent wherein each alkyl is of up to 5 carbon atoms and wherein cyclic amino has up to 6 carbon atoms, or an alkanoylamino, alkoxycarbonylamino or alkoxycarbonyl substituent each of up to 6 carbon atoms or an arylalkoxycarbonyl substituent of up to 10 carbon atoms, or an aryl or heterocyclyl substituent;

wherein either $R^5$ is hydrogen or alkyl of up to 5 carbon atoms which is unsubstituted or which bears an aryl substituent or $R^5$ is joined together with $R^6$ as defined below;

wherein either $R^6$ is hydrogen, aryl or heterocyclic, or alkyl of up to 5 carbon atoms which is unsubstituted or which bears a hydroxy, aryl or heterocyclic substituent;

or $R^6$ and $R^5$ are joined together to form alkylene or alkenylene of 2 to 5 carbon atoms; or an oxa-, thia- or aza-derivative of said alkylene or alkenylene; or a hydroxy- or oxo-substituted derivative of said alkylene or alkenylene;

or $R^6$ and $R^{16}$, or $R^6$, $R^{16}$ and $R^5$, or $R^6$ and $R^{10}$ are joined together as defined below;

wherein $R^{16}$ is hydrogen or alkyl of up to 5 carbon atoms; or $R^{16}$ has the formula $Q^1$—$R^{10}$ as defined below; or $R^6$ and $R^{16}$ are joined together to form alkylene of 2 to 5 carbon atoms (that is, to form a spirocycloalkyl group);

or $R^{16}$ together with the first carbon atom of $R^6$ form a double bond wherein $R^6$ is otherwise alkyl, or wherein $R^6$ is otherwise substituted alkyl as defined above, or wherein $R^6$ and $R^5$ are otherwise joined together as defined above (that is, so that $R^5$, $R^6$ and $R^{16}$ together form alkylidene);

wherein $Q^1$ and $Q^2$, which may be the same or different, each is carbonyl (—CO—) or methylene (—CH$_2$—);

and wherein either $R^{10}$ and $R^{20}$, which may be the same or different, is hydroxy, amino, hydroxyamino, aryloxy, arylthio, alkoxy, alkenyloxy, cycloalkoxy, alkylamino, dialkylamino, cyclic amino, hydroxyalkoxy, acyloxyalkoxy, aminoalkoxy, alkylaminoalkoxy, dialkylaminoalkoxy, cyclicaminoalkoxy, alkanoylaminoalkoxy, alkoxycarbonylmethoxy, aminoalkylamino, alkylaminoalkylamino, dialkylaminoalkylamino, cyclic aminoalkylamino, alkanoylaminoethylamino or arylalkoxy wherein each alkyl, alkanoyl, alkoxycarbonyl, alkoxy, alkenyloxy or cycloalkoxy has up to 5 carbon atoms and wherein cyclic amino has up to 6 carbon atoms;

or wherein $R^{10}$ and $R^6$ are joined together such that $R^{10}$ is oxygen (—O—) joined to the terminal carbon atom of $R^6$ when it is alkyl;

or a salt thereof wherein appropriate.

It will be observed that there are various potentially asymmetrical carbon atoms in the amide of the invention, in particular the carbon atom which bears the substituent $R^2$, the carbon atom which bears the substituent $R^4$ when this substituent is other than hydrogen, and the carbon atom which bears the substituents $R^6$ and $R^{16}$ when these are different one from the other, and that the amide may therefore exist in racemic and optically active forms. It is to be understood that this invention encompasses the racemic form and any optically-active form which possesses ACE-inhibiting properties, it being a matter of common general knowledge how an optically active compound may be prepared and how the ACE-inhibiting properties of a compound may be measured.

It is to be understood that the various definitions of $R^1$ and other R values in the last two preceding paragraphs and hereinafter refer to the present invention and not to the substituents defined in European Specification No. 12401.

A suitable value for $R^1$ or $R^6$ when it is aryl, or for the aryl substituent in the group $R^2$, $R^4$, $R^5$, $R^6$ or $R^{12}$ when said group is alkyl substituted by aryl, or for the aryl substituent in $R^{10}$ or $R^{20}$ when it is arylalkoxy, that is, alkoxy substituted by aryl, is, for example, unsubstituted phenyl or naphthyl, or phenyl or naphthyl substituted by one or more substituents selected from halogen, for example fluoro, chloro, bromo and iodo, alkyl, alkenyl, alkynyl, alkylthio and alkoxy each of up to 5 carbon atoms, for example methyl, ethyl, t-butyl, allyl, propargyl, methylthio, methoxy, ethoxy and isopropoxy, and hydroxy, methylenedioxy, amino, nitro, cyano, carboxy, carbamoyl, sulphamoyl, trifluoromethoxy and trifluoromethyl, aryl, for example phenyl and p-chlorophenyl, arylalkoxy, for example benzyloxy, and substituents of the formula:

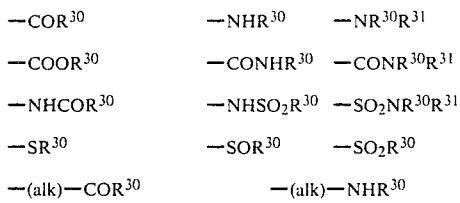

wherein either $R^{30}$ and $R^{31}$, which may be the same or different, each is phenyl, or trifluoromethyl, or alkyl of up to 5 carbon atoms, for example methyl, ethyl or n-propyl, which is unsubstituted or which is substituted by phenyl, or $R^{30}$ and $R^{31}$ are joined such that together with the adjacent nitrogen atom they form pyrrolidino, carboxypyrrolidino, alkoxycarbonylpyrrolidino, piperidino, 4-methylpiperazino or morpholino, and wherein -alk- is alkylene of 1 to 4 carbon atoms.

A suitable value for $R^1$ or $R^6$ when it is heterocyclic, or for the heterocyclic substituent in $R^4$ or $R^6$ when it is alkyl substituted by heterocyclic, is, for example, a 5- or 6-membered heterocyclic ring containing 1 or 2 heteroatoms selected from oxygen, nitrogen and sulphur, which ring may be saturated or unsaturated, and which ring may optionally contain one or more oxo, alkyl, alkoxy, arylalkyl or halogen substituents, for example methyl, methoxy, benzyl, chloro or bromo substituents, and which heterocyclic ring may also be fused to a benzene ring. Suitable heterocyclic rings are, for example, pyridyl, furyl, 5-methyl-2-furyl, thienyl, 5-chloro-2-thienyl, 5-methyl-2-thienyl, pyrrolyl, 1-methyl-2-pyrrolyl, 1,5-dimethyl-2-pyrrolyl, 2,5-dimethyl-3-pyrrolyl, imidazolyl, thiazolyl, isoxazolyl, indolyl, 1-methyl-3-indolyl, 1-benzyl-3-indolyl, benzofuryl, benzothienyl, quinolyl or benzimidazolyl.

A suitable value for $R^1$ when it is halogeno or for the halogeno substituent in $R^4$ is, for example, fluoro or chloro.

A suitable value for $R^2$, $R^3$, $R^4$, $R^5$, $R^6$, $R^{11}$, $R^{12}$, $R^{13}$, $R^{14}$, $R^{16}$ or $R^{21}$ when it is alkyl is, for example, methyl, ethyl, n-propyl, isopropyl or isobutyl.

A suitable value for $R^5$ when it is alkyl is, for example, methyl or ethyl.

A suitable value for $A^1$ is, for example, a direct bond or methylene, ethylene, ethylidene (—CHCH$_3$—), 1-methyl-ethylidene [—C(CH$_3$)$_2$—], 1-methylethylene, decamethylene, pentadecamethylene, vinylene, cyclohexene-1,4-diyl or cyclohex-2-ene-1,4-diyl.

A suitable value for alkylene formed by $R^6$ and $R^{16}$ joined together or by $R^{13}$ and $R^{14}$ joined together is, for example ethylene, trimethylene, 2,2-dimethyltrimethylene or tetramethylene.

A suitable value for $A^2$ is, for example, methylene, ethylene, 2-methylethylene, 2,2-dimethylethylene, trimethylene, tetramethylene, ethylidene, 1-methylethylidene, vinylene or methine.

A suitable value for $A^3$ is a direct link, methylene or ethylene.

A suitable value for $R^{10}$ or $R^{20}$ when it is alkoxy, or for the alkoxy substituent in $R^4$ when said group is alkyl substituted by alkoxy is, for example, methoxy, ethoxy, n-propoxy, isopropoxy, n-butoxy or t-butoxy.

A suitable value for $R^{10}$ or $R^{20}$ when it is alkylamino, dialkylamino or cyclic amino, or for such a substituent in $R^4$ wherein said group is alkyl bearing such a substituent is, for example, methylamino, ethylamino, dimethylamino, pyrrolidino, piperidino, 4-methylpiperazino or morpholino.

A suitable value for the alkylthio, alkanoylamino, alkoxycarbonylamino, alkoxycarbonyl or arylalkoxycarbonyl substituent in $R^4$ when it is alkyl substituted by alkylthio, alkanoylamino, alkoxycarbonylamino, alkoxycarbonyl or arylalkoxycarbonyl is, for example, methylthio, acetamido, t-butoxycarbonylamino, methoxycarbonyl or benzyloxycarbonyl.

A suitable value for alkylene or alkenylene formed by $R^5$ and $R^6$ joined together is, for example, ethylene, trimethylene, tetramethylene, pentamethylene, propenylene (—CH$_2$—CH=CH—), but-1-enylene (—CH$_2$CH$_2$—CH=CH—), 2-oxatrimethylene (—CH$_2$—O—CH$_2$—), 2-thiatrimethylene (—CH$_2$—S—CH$_2$—), 3-oxatetramethylene (—CH$_2$CH$_2$—O—CH$_2$—), 3-thiatetramethylene (—CH$_2$CH$_2$—S—CH$_2$—), 3-azatetramethylene (—CH$_2$CH$_2$—NH—CH$_2$—), 3-methyl-3-azetetramethylene

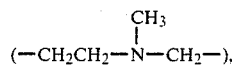

2-hydroxy-trimethylene (—CH$_2$CHOHCH$_2$—); 1-oxotrimethylene (—COCH$_2$CH$_2$—) or 1-oxotetramethylene (—COCH$_2$CH$_2$CH$_2$—).

A suitable value for alkylidene formed by $R^5$, $R^6$ and $R^{16}$ joined together is, for example, propan-1-yl-3-ylidene (—CH$_2$CH$_2$CH=).

A suitable value for $R^{10}$ or $R^{20}$ when it is aryloxy is, for example, unsubstituted phenoxy or phenoxy substituted by one or more substituents selected from those stated above as suitable substituents in aryl.

A suitable value for $R^{10}$ or $R^{20}$ when it is arylthio is, for example, unsubstituted phenylthio or phenylthio substituted by one or more substituents selected from those stated above as possible substituents in aryl.

A suitable value for $R^{10}$ or $R^{20}$ when it is alkenyloxy, cycloalkoxy, hydroxyalkoxy or acyloxyalkoxy is, for example, allyloxy, cyclopentyloxy, cyclohexyloxy, 2-hydroxyethoxy, 3-hydroxypropoxy or pivaloyloxymethoxy.

A suitable value for $R^{10}$ or $R^{20}$ when it is aminoalkoxy, alkylaminoalkoxy, dialkylaminoalkoxy, cyclic aminoalkoxy, alkanoylaminoalkoxy, aminoalkylamino, alkylaminoalkylamino, dialkylaminoalkylamino or cyclic aminoalkylamino is, for example, ethoxy, propoxy, ethylamino or propylamino substituted in the 2- or 3-position respectively by amino, methylamino, ethylamino, dimethylamino, pyrrolidino, piperidino, 4-methylpiperazino, morpholino or acetamido. Alternatively, $R^{10}$ or $R^{20}$ when cyclic aminoalkoxy or aminoalkylamino may be a cyclic amine bearing an oxy- or amino-substituent on one of the carbon atoms of the cyclic amine, for example 1-methylpiperidin-4-yloxy or 1-methylpiperidin-4-ylamino.

A suitable value for $R^{10}$ or $R^{20}$ when it is alkoxycarbonylmethoxy is, for example, methoxycarbonylmethoxy.

When $Q^1$ is carbonyl and $R^6$ and $R^{10}$ are joined together the group —CR$^6$R$^{16}$—Q$^1$—R$^{10}$— may be, for example, the lactone group 2-oxotetrahydrofuran-3-yl or 2-oxotetrahydropyran-3-yl.

Preferably X, $Q^1$ and $Q^2$ are all carbonyl and $R^3$ and $R^{16}$ are both hydrogen.

More preferably, the group represented by the partial structure

—NR$^3$—CHR$^4$—CO—NR$^5$—CR$^6$R$^{16}$—Q$^1$—R$^{10}$ is a natural dipeptide unit or a C-terminal simple ester or amide there of, especially L-alanyl-L-proline, L-lysyl-L-proline, L-valyl-L-tryptophan or L-glutamyl-L-proline or a simple ester or amide thereof.

A preferred amide derivative of the invention has the formula:

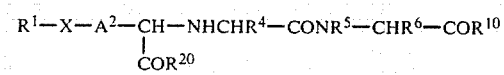

wherein $R^1$ is aryl or heterocyclic as defined above, wherein X has the formula —CO— or

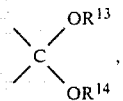

wherein $R^{13}$ and $R^{14}$ have the meanings stated above, wherein $A^2$ is alkylene of up to 5 carbon atoms, wherein $R^4$ is hydrogen or alkyl of up to up to 5 carbon atoms which is unsubstituted or which bears an amino, alkoxycarbonylamino, carboxy or alkoxycarbonyl substituent each of up to 5 carbon atoms, wherein $R^5$ is hydrogen or alkyl and $R^6$ is hydrogen or alkyl of up to 5 carbon atoms which is unsubstituted or which bears an indolyl substituent, or $R^5$ and $R^6$ together form alkylene or thiaalkylene of 3 or 4 carbon atoms, and wherein $R^{10}$ and $R^{20}$, which may be the same or different, each is hydrogen or alkoxy of up to 5 carbon atoms; or a salt thereof where appropriate.

In particular, $R^1$ is phenyl, biphenylyl or naphthyl which is unsubstituted or which bears one or two halogen, alkyl, alkoxy or dialkylamino substituents, for example fluoro, chloro, bromo, methyl, methoxy, isopropoxy or dimethylamino substituents, or $R^1$ is thienyl, furyl, pyrrolyl, pyridyl, benzothienyl, benzofuryl or indolyl which is unsubstituted or which bears one or two halogen or alkyl substituents, for example chloro or methyl substituents; X is carbonyl, ethylenedioxymethylene or 2,2-dimethyltrimethylene-1,3-dioxymethylene; $A^2$ has the formula —(CH$_2$)$_n$— wherein n is 1, 2, 3 or 4; $R^4$ is hydrogen, methyl, isopropyl, 4-aminobutyl, 4-(t-butoxycarbonylamino)butyl, 2-carboxyethyl, 2-methoxycarbonylethyl or 2-ethoxycarbonylethyl; $R^5$ is hydrogen or isopropyl and $R^6$ is hydrogen or 3-indolylmethyl, or $R^5$ and $R^6$ together form trimethylene or 2-thiatrimethylene; and $R^{10}$ and $R^{20}$, which may be the same or different, each is hydroxy, methoxy, ethoxy, propoxy or t-butoxy.

A preferred amide derivative of the invention wherein $R^1$ is simple aryl, for example unsubstituted phenyl, wherein X is carbonyl and wherein $A^2$ is methylene, although possessing good ACE-inhibiting activity, is however relatively chemically unstable, the process for manufacture of such a compound as hereinafter described being fairly readily reversible in solution. This instability can to some extent be overcome by having an appropriate substituent, for example a para-dimethylamino substituent in the phenyl ring. Furthermore, wherein $R^1$ is a nitrogen-containing heterocyclic group and the nitrogen atom is one or two double-bonds removed from the carbonyl group —X— there is considerable improvement in stability. When $A^2$ is such that more than one carbon atom separates the groups —X— and —CH(COR$^{20}$)— such instability does not occur.

One particularly preferred amide derivative of the invention has the formula:

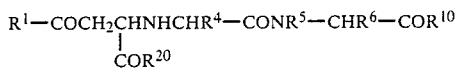

wherein $R^1$ is heterocyclic, and $R^4$, $R^5$, $R^6$, $R^{10}$ and $R^{20}$ have the meanings stated above. Especially $R^4$ is hydrogen or alkyl, aminoalkyl or carboxyalkyl, for example methyl, isopropyl, 4-aminobutyl or 2-carboxyethyl, $R^5$ is hydrogen and $R^6$ is 3-indolylmethyl or $R^5$ and $R^6$ together form trimethylene or 2-thiatrimethylene, and $R^{10}$ and $R^{20}$, which may be the same or different, each is hydroxy or alkoxy of up to 5 carbon atoms, for example methoxy or ethoxy. In this group $R^1$ may be 2-thienyl, 5-methyl-2-thienyl, 3-thienyl or 2-furyl, and especially $R^1$ is 2-pyrrolyl, 1-methyl-2-pyrrolyl, 1,5-dimethyl-2-pyrrolyl, 2,5-dimethyl-3-pyrrolyl, 3-indolyl, 1-methyl-3-indolyl or 1-benzyl-3-indolyl.

A second particularly preferred amide derivative of the invention has the formula:

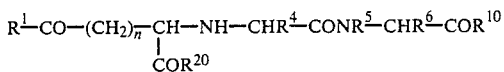

wherein $R^1$ is aryl or heterocyclic, n is 2, 3 or 4 and $R^4$, $R^5$, $R^6$, $R^{10}$ and $R^{20}$ have the meanings stated above, especially the meanings stated in the last paragraph above. $R^1$ may be phenyl, 4-biphenyl or naphthyl, which may be unsubstituted or bear a halogen, alkyl or alkoxy substituent, for example a fluoro, chloro, bromo, methyl or methoxy substitutent, or $R^1$ may be thienyl, furyl, pyrrolyl, pyridyl, benzothienyl, benzofuryl or indolyl which may be unsubstituted or which may bear a halogen or alkyl substituent, for example a chloro or methyl substituent. In this group $R^1$ is preferably one of the abovementioned heterocyclic groups, and n is preferably 3.

In both particularly preferred amide derivatives of the invention described in the last two paragraphs the group $$-NHCHR^4-CONR^5-CHR^6-COR^{10}$$

is preferably L-alanyl-L-proline, L-lysyl-L-proline, L-glutamyl-L-proline, L-valyl-L-tryptophan or N-(L-alanyl)thiazolidine-(R)-4-carboxylic acid or a monoalkyl ester thereof, or a di-alkyl ester of the glutamyl-proline, or a salt thereof.

Specific compounds of the invention are hereinafter described in the Examples. Of these, preferred compounds by virtue of their high levl of ACE-inhibitory activity are:

N-[1-carboxy-3-(1-methylpyrrol-2-yl)-3-oxopropyl]-L-alanyl-L-proline and the diethyl ester thereof;
N-[1-ethoxycarbonyl-3-oxo-3-(pyrrol-2-yl)propyl]-L-alanyl-L-proline ethyl ester;
N-[3-(2,5-dimethylpyrrol-3-yl)-1-ethoxycarbonyl-3-oxopropyl]-L-alanyl-L-proline ethyl ester;
N-[3-(1,5-dimethylpyrrol-2-yl)-1-ethoxycarbonyl-3-oxopropyl]-L-alanyl-L-proline ethyl ester;
N-[1-carboxy-3-(3-indolyl)-3-oxopropyl]-L-alanyl-L-proline and the diethyl ester thereof;
$N^1$-[1-carboxy-3-(1-methylpyrrol-2-yl)-3-oxopropyl]-L-lysyl-L-proline;
$N^1$-[1-carboxy-3-(3-indolyl)-3-oxopropyl]-L-lysyl-L-proline;
N-[1-methoxycarbonyl-5-oxo-5-phenylpentyl]-L-alanyl-L-proline methyl ester;
N-[1-carboxy-5-oxo-5-(2-thienyl)pentyl]-L-alanyl-L-proline and the dimethyl ester thereof and the diethyl ester thereof;
N-[1-ethoxycarbonyl-5-oxo-5-(3-thienyl)pentyl]-L-alanyl-L-proline ethyl ester;
N-[1-ethoxycarbonyl-5-(2-furyl)-5-oxopentyl]-L-alanyl-L-proline ethyl ester; and
$N^1$-[1-carboxy-5-oxo-5-(2-thienyl)pentyl]-L-lysyl-L-proline;
and the salts thereof where appropriate.

A suitable salt of an amide derivative of the invention wherein $R^{10}$ or $R^{20}$ is hydroxy is, for example, an alkali metal of alkaline earth metal salt, for example a sodium, potassium, calcium or magnesium salt, or an ammonium or dicyclohexylamine salt.

Alternatively, a salt may be an acid-addition salt of the amino-function $-NR^3-$, for example a hydrochloride or trifluoroacetate salt.

An amide derivative of the invention may be manufactured by any chemical process known to be suitable for preparing compounds of related chemical types.

One process for the manufacture of an amide derivative of the invention wherein $Q^2$ is carbonyl, $R^{20}$ is hydrocarbonoxy and $A^2$ is methylene comprises the reaction of a compound of the formula:

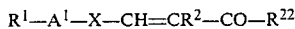

wherein $R^1$, $A^1$ and $R^2$ have the meanings stated above and wherein $R^{22}$ is hydrocarbonoxy, with a compound of the formula

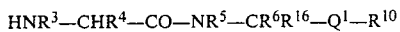

wherein $R^3$, $R^4$, $R^5$, $R^6$, $R^{10}$, $R^{16}$ and $Q^1$ have the meanings stated above.

The reaction may be carried out in an inert diluent or solvent, for example dichloromethane, ethylene dichloride or dimethylformamide, and it is preferably carried out at laboratory temperature.

The process is particularly valuable for preparing an amide derivative of the invention wherein $A^1$ is a direct link, X is carbonyl and $R^1$ is aryl or heterocyclic. The starting material in such a case may be obtained by the reaction of a compound of the formula

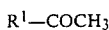

wherein $R^1$ has the meaning stated above, with glyoxylic acid or an ester thereof, followed by esterification if required, or by the reaction of a compound of the formula

wherein $R^1$ has the meaning above, and Z is a halogeno group, for example the chloro or bromo group, with a phosphorane of the formula

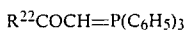

wherein $R^{22}$ has the meaning stated above.

A second process for the manufacture of an amide derivative of the invention wherein $Q^2$ is carbonyl and $R^2$ and $R^3$ are both hydrogen comprises the reaction of a compound of the formula:

$$R^1-A^1-X-A^2-CO-COR^{22}$$

wherein $R^1$, $R^{22}$, $A^1$, $A^2$ and X have the meanings stated above, with a compound of the formula:

$$H_2N-CHR^4-CO-NR^5-CR^6R^{16}-Q^1-R^{10}$$

wherein $R^4$, $R^5$, $R^6$, $R^{10}$, $R^{16}$ and $Q^1$ have the meanings stated above, under dehydrating and reducing conditions.

The dehydrating conditions are preferably provided by molecular sieve and the reducing conditions are preferably provided by an alkali metal cyanoborohydride, for example sodium cyanoborohydride, or by hydrogen in the presence of a catalyst. The reaction is preferably carried out in an alcoholic solution, for example in ethanol solution.

The last-mentioned process is particularly valuable for preparing an amide derivative of the invention wherein $A^2$ is —$(CH_2)_n$— wherein n is 2, 3 or 4, and especially wherein also $A^1$ is a direct link, X is protected carbonyl and $R^1$ is aryl or heterocyclic. The starting material in such a case may be obtained by converting a nitrile of the formula:

$$R^1-X^1-A^2-CN$$

wherein $R^1$ and $A^2$ have the meanings stated above and wherein $X^1$ is protected carbonyl, to the corresponding compound of the formula $$R^1-X^1-A^2-COCOR^{22}$$

wherein $R^1$, $X^1$, $A^2$ and $R^{22}$ have the meanings stated above, by reaction successively with methyl methylthiomethyl sulphoxide and sodium hydride, then with cuprous chloride and cuprous oxide, and then with an alcohol of the formula $R^{22}$—H.

Alternatively, the starting material may be obtained by the reaction of a Grignard reagent of the formula $$R^1-X^1-A^2-Mg-Z$$

wherein $R^1$, $X^1$, $A^2$ and Z have the meanings stated above, with a dialkyl oxalate.

A third process for the manufacture of an amide derivative of the invention wherein $Q^2$ is carbonyl and $R^{20}$ is $R^{22}$ as defined above, and wherein $R^2$ is $Q^2R^{22}$, comprises the reaction of a compound of the formula:

$$R^1-A^1-X-A^2-Z^1$$

wherein $R^1$, $A^1$, $A^2$ and X have the meanings stated above and $Z^1$ is a displaceable group, with a compound of the formula:

$$(R^{22}CO)_2CH-NR^3-CHR^4-NR^5-CR^6R^{16}-Q^1-R^{10}$$

wherein $R^3$, $R^4$, $R^5$, $R^6$, $R^{10}$, $R^{16}$, $R^{22}$ and $Q^1$ have the meanings stated above, in the presence of a base.

The displaceable group $Z^1$ may be, for example, a halogeno group or a dialkylamino or trialkylammonium group. The reaction may be carried out in a diluent or solvent, for example methanol, ethanol or tetrahydrofuran. The base may be, for example, an alkali metal hydride, alkoxide or carbonate, depending upon the particular reactant and solvent.

This process is particularly valuable for preparing an amide derivative of the invention wherein $A^2$ is ethylene, and especially wherein also $A^1$ is a direct link, X is carbonyl and $R^1$ is aryl or heterocyclic. The starting material in such a case may be obtained by a Mannich reaction of a compound of the formula $$R^1-COCH_3$$

wherein $R^1$ has the meaning stated above, with formaldehyde and a dialkylamine, to provide a compound wherein $Z^1$ is dialkylamino, and this compound may be alkylated to provide a compound wherein $Z^1$ is trialkylammonium. When $Z^1$ is halogeno the starting material may be obtained by a Friedel-Crafts reaction of a halopropionyl halide with the appropriate aromatic or heterocyclic compound $R^1H$.

An amide derivative of the invention wherein $R^{10}$ or $R^{20}$ is other than hydroxy (that is, wherein $Q^1$—$R^{10}$ or $Q^2$—$R^{20}$ forms an ester or amide group) may be obtained from the corresponding acid wherein $Q^1$—$R^{10}$ or $Q^2$—$R^{20}$ is —COOH by conventional means of ester or amide formation. In particular, a lower alkyl ester may be obtained by reaction of the acid with a diazoalkane, or by reaction with an alkanol in the presence of an anhydrous mineral acid such as hydrogen chloride or sulphuric acid.

An amide derivative of the invention wherein $Q^1$ and $Q^2$ are both carbonyl and $R^{10}$ and $R^{20}$ are both hydroxy may be obtained by the hydrolysis of the corresponding amide derivative of the invention wherein either or both of $R^{10}$ and $R^{20}$ is alkoxy, or, when $R^{10}$ or $R^{20}$ is t-butoxy, by the acid-catalysed cleavage of said compound, for example with trifluoroacetic acid, or when $R^{10}$ or $R^{20}$ is benzyloxy, by the catalytic hydrogenolysis of said compound.

An amide derivative of the invention wherein X is a protected carbonyl group, for example an alkylenedioxymethylene group, may be converted into the corresponding compound wherein X is carbonyl by acid-catalysed hydrolysis.

An amide derivative of the invention wherein $R^2$ is —$COR^{22}$ wherein $R^{22}$ has the meaning stated above may be converted into the corresponding compound wherein $R^2$ is hydrogen by hydrolysis and decarboxylation.

An amide derivative of the invention wherein X is hydroxymethylene or hydroxyaminomethylene may be obtained by the reduction, for example with an alkali metal borohydride, of the corresponding amide derivative of the invention wherein X is carbonyl or oximinomethylene, and an amide derivative of the invention wherein X is oximinomethylene may be obtained by the reaction of the corresponding amide derivative of the invention wherein X is carbonyl with hydroxylamine or an O-substituted hydroxylamine derivative.

As stated above, an amide derivative of the invention possesses ACE-inhibiting properties. ACE is the enzyme which converts angiotensin I to angiotensin II. The ACE-inhibiting properties of an amide derivative of the invention may be demonstrated by its ability to prevent the cleavage of angiotensin I or of a synthetic peptide related to angiotensin I by ACE.

Angiotensin II is a potent constrictor of vascular smooth muscle, and is therefore involved in the control of blood pressure. A compound which prevents conversion of angiotensin I to angiotensin II will therefore lower circulating levels of angiotensin II and cause a fall in blood pressure. An amide derivative of the invention may therefore be used to lower blood pressure in a warm-blooded animal (including a human). At a dose of an amide derivative of the invention which lowers blood pressure in an experimental animal, for example a rat, no symptoms of toxicity are apparent.

An amide derivative of the invention may be administered to a warm-blooded animal, including man, in the form of a pharmaceutical composition comprising as active ingredient at least one amide derivative of the invention, or a salt thereof, in association with a pharmaceutically-acceptable diluent or carrier therefor.

A suitable composition is, for example, a tablet, capsule, aqueous or oily solution or suspension, emulsion, dispersible powder, spray or aerosol formulation.

The pharmaceutical composition may contain, in addition to the amide derivative of the invention, one or more drugs selected from diuretics, for example bendrofluazide, chlorothiazide, hydrochlorothiazide, furosemide, amiloride and chlorthalidone; and other hypotensive agents, for example β-adrenergic blocking agents, for example atenolol and propranolol.

When used for the treatment of hypertension in man, it is expected that the amide derivative of the invention would be given to man at a total oral dose of between 10 mg. and 500 mg. daily, at doses spaced at 6–12 hourly intervals, or at an intravenous dose of between 1.0 mg. and 50 mg.

Preferred oral dosage forms are tablets or capsules containing between 10 mg. and 100 mg. of active ingredient. Preferred intravenous dosage forms are sterile aqueous solutions of active ingredient containing between 0.1% and 1% w/v of active ingredient.

The invention is illustrated but not limited by the following Examples. In these Examples the following general procedures were adopted:

CHROMATOGRAPHY

1. Unless otherwise stated, column chromatography on silica gel was carried out using Merck Art. 7734 and on Sephadex using Sephadex LH20.
2. "Flash" chromatography was carried out on silica gel using Merck Art. 9385.
3. Medium pressure liquid (MPL) chromatography was carried out using a Gilson Model 302 pump and a Model 111 UV detector, and a Kipp+Zouen BD8 Multirange recorder.

CONFIRMATION OF STRUCTURES

All final compounds falling within the scope of the invention were examined by proton magnetic resonance spectroscopy using either a Varian EM 390, Bruker HX90E or JEOL FX 90Q machine, and by mass spectrometry using a KRATOS MS 902 for election impact spectra or Vacuum Generators 1212 operating in the electron impact/chemical ionisation mode. Fast atom bombardment (FAB) spectra were obtained on a KRATOS MS9 modified for FAB by Vacuum Generators.

In all cases the spectra confirmed that the named compound had been obtained. Details of these spectra are presented in Example 18 to illustrate the actual figures for the compound described therein. Appropriate figures were obtained in all other cases.

ISOMERS

All compounds in which the substituent $R^2$ is hydrogen have an asymmetrical centre at the carbon atom bearing that substituent, and there are asymmetrical centres of fixed configuration at the carbon atoms bearing the substituents $R^4$ and $R^6$. Unless otherwise stated all compounds were isolated as mixtures of isomers in respect of the $R^2$ asymmetrical centre. Where separation of isomers was achieved as hereinafter described, both isomers possess ACE-inhibiting activity but one isomer was usually more active than the other.

EXAMPLE 1

A solution of L-alanyl-L-proline t-butyl ester (2.1 g.) and t-butyl 4-oxo-4-phenylbut-trans-2-enoate (2.0 g.) in dichloromethane (30 ml.) was stirred at laboratory temperature for 18 hours and then evaporated to dryness under reduced pressure. The residue was purified by chromatography on a silica gel column using a 3:1 v/v mixture of dichloromethane and ethyl acetate as eluant, and there was thus obtained as an oil N-[1-t-butoxycarbonyl-3-oxo-3-phenylpropyl]-L-alanyl-L-proline t-butyl ester.

The t-butyl 4-oxo-4-phenylbut-trans-2-enoate used as starting material was obtained as follows:

Isobutylene was bubbled for 20 minutes through a solution of 4-oxo-4-phenylbut-trans-2-enoic acid (5 g.) and concentrated sulphuric acid (0.1 ml.) in dichloromethane (100 ml.) which was kept anhydrous at laboratory temperature, and the mixture was kept at laboratory temperature for 4 days and then poured into saturated aqueous sodium carbonate solution (100 ml.). The organic layer was separated, dried over magnesium sulphate and evaporated to dryness, and the residue was purified by chromatography on a silica gel column using a 1:1 v/v mixture of dichloromethane and petroleum ether (b.p. 40°–60° C.) as eluant. There was thus obtained, as an oil, t-butyl 4-oxo-4-phenylbut-trans-2-enoate.

EXAMPLE 2

The process described in Example 1 was repeated using ethyl 4-oxo-4-phenylbut-trans-2-enoate and L-alanyl-L-proline ethyl ester hydrochloride (together with one molecular proportion of triethylamine to neutralise the hydrochloride) as starting materials, and using dichloromethane as reaction solvent. There was thus obtained N-[1-ethoxycarbonyl-3-oxo-3-phenylpropyl]-L-alanyl-L-proline ethyl ester as an oil.

EXAMPLE 3

The process described in Example 2 was repeated using benzyl esters in place of ethyl esters in both starting materials. There was thus obtained N-[1-benzyloxycarbonyl-3-oxo-3-phenylpropyl]-L-alanyl-L-proline benzyl ester as an oil.

EXAMPLE 4

A solution of ethyl 4-oxo-4-phenylbut-trans-2-enoate (1.9 g.), L-alanyl-L-proline (1.74 g.) and triethylamine (1.4 ml.) in dimethylformamide (30 ml.) was stirred at laboratory temperature for 18 hours and then evaporated to dryness under reduced pressure at a temperature less than 30° C. The residue was purified by chromatography on a silica gel column using a 9:1 v/v mixture of dichloromethane and methanol as eluant, and there was thus obtained as an oil N-[1-ethoxycarbonyl-3-oxo-3-phenylpropyl]-L-alanyl-L-proline.

EXAMPLE 5

A mixture of N-[1-t-butoxycarbonyl-3-oxo-3-phenylpropyl]-L-alanyl-L-proline t-butyl ester (Example 1; 0.65 g.) and trifluoroacetic acid (20 ml.) was kept at laboratory temperature for 2 hours and the trifluoroacetic acid was removed by evaporation under reduced pressure at a temperature not exceeding 35° C. Dichloromethane and toluene (15 ml. each) were added and the mixture was evaporated to dryness under reduced pressure below 35° C. The residue was purified by chromatography on a silica gel column using successively a 9:1 v/v, then a 7:3 v/v, then a 1:1 v/v mixture of dichloromethane and methanol as eluant. There was thus obtained, as product eluted by the last-mentioned solvent mixture, the trifluoroacetate salt of N-[1-carboxy-3-oxo-3-phenylpropyl]-L-alanyl-L-proline.

EXAMPLE 6

The process described in Example 1 or 2 was repeated using the appropriate L-alanyl-L-proline ester and the appropriate 4-oxo-4-substituted-phenylbut-trans-2-enoic ester as starting materials, and there were thus obtained the compounds described in the following table:

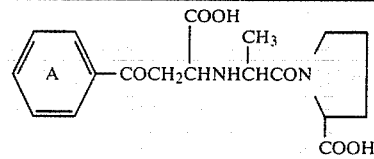

| Ring A substituent | $R^{17}$, $R^{27}$ |
| --- | --- |
| 4-benzyloxy | t-butyl |
| 4-benzyloxy | ethyl |
| 4-methoxy | t-butyl |
| 4-methoxy | ethyl |
| 3,4-dimethoxy | t-butyl |
| 3,4-dimethoxy | ethyl |
| 4-isopropoxy | t-butyl |
| 4-isopropoxy | ethyl |

The 4-oxo-4-substituted-phenyl-trans-2-enoate esters used as starting materials were obtained by heating the appropriate substituted acetophenone with glyoxylic acid in acetic acid solution to give the 4-oxo-4-substituted-phenylbut-trans-2-enoic acid, and then preparing the t-butyl ester with isobutylene as described in Example 1, or preparing the ethyl ester by reaction with ethanol in dichloromethane solution in the presence of dicyclohexylcarbodiimide and 4-dimethylaminopyridine.

EXAMPLE 7

The process described in Example 5 was repeated using the di-t-butyl esters described in Example 6 as starting materials. There were thus obtained the trifluoroacetate salts of the compounds described in the following table:

| Ring A substituent |
| --- |
| 4-hydroxy* |
| 4-methoxy |
| 3,4-dimethoxy |
| 4-isopropoxy |

*The 4-benzyloxyphenyl compound was used as starting material, the benzyl group being removed by the trifluoroacetic acid treatment.

EXAMPLE 8

Hydrogen chloride was bubbled through a solution of N-[3-(4-benzyloxyphenyl)-3-oxo-1-t-butoxycarbonyl-propyl]-L-alanyl-L-proline t-butyl ester (Example 6; 0.2 g.) in dichloromethane (30 ml.) for 30 minutes, and the mixture was kept at laboratory temperature for 9 hours and then evaporated to dryness under reduced pressure. There was thus obtained as residue N-[3-(4-benzyloxyphenyl)-1-carboxy-3-oxopropyl]-L-alanyl-L-proline dihydrochloride.

EXAMPLE 9

Triethylamine (0.02 g.) was added to a stirred solution of t-butyl 4-p-dimethylaminophenyl-4-oxobut-trans-2enoate (1.37 g.) and L-alanyl-L-proline t-butyl ester (1.21 g.) in dichloromethane, and the mixture was stirred at laboratory temperature for 40 hours and then evaporated to dryness under reduced pressure. The residue was purified by chromatography on a silica gel column using a 9:1 v/v mixture of dichloromethane and ethyl acetate as eluant. There was thus obtained as an oil N-[3-p-dimethylaminophenyl-3-oxo-1-t-butoxycarbonylpropyl]-L-alanyl-L-proline t-butyl ester.

A mixture of the above compound (0.7 g.) and trifluoroacetic acid (10 ml.) was kept at laboratory temperature for 2 hours, evaporated to dryness under reduced pressure, and toluene was repeatedly added and removed by evaporation under reduced pressure to remove all trace of trifluoroacetic acid. There was thus obtained as an oil N-[1-carboxy-3-p-dimethylaminophenyl-3-oxopropyl]-L-alanyl-L-proline ditrifluoroacetate.

The t-butyl 4-p-dimethylaminophenyl-4-oxobut-trans-2-enoate used as starting material was obtained as follows:

Dimethylamine was bubbled for 16 hours through a solution of p-fluoroacetophenone (78.2 g.) in dimethyl sulphoxide (350 ml.) which was maintained at 80° C., argon was then bubbled vigorously through the mixture to remove the excess of dimethylamine, and the mixture was poured onto crushed ice (3000 ml.). The mixture was filtered and the solid residue was crystallised from a 1:1 v/v mixture of petroleum ether (b.p. 60°–80° C.) and diethyl ether. There was thus obtained p-dimethylaminoacetophenone.

A mixture of the above compound (32.6 g.), glyoxylic acid (20.24 g.) and acetic acid (50 ml.) was heated under reflux for 16 hours, cooled, diluted with diethyl ether (50 ml.) and the solvent was decanted from the black tar. The tar was purified by chromatography on a silica gel column (1000 g.) using a 19:1 v/v mixture of dichloromethane and methanol as eluant, followed by MPL chromatography on a silica column using a 40:1 v/v mixture of dichloromethane and methanol as eluant.

There was thus obtained 4-p-dimethylaminophenyl-4-oxobut-trans-2-enoic acid.

N,N$^1$-Dicyclohexylcarbodiimide (0.564 g.) and 4-dimethylaminopyridine (0.033 g.) were added to a stirred solution of the above compound (0.6 g.) in t-butanol (10 ml.) which was cooled to 0° C., and the mixture was allowed to warm up to laboratory temperature and stirred at that temperature for 240 hours. The excess of t-butanol ws removed by evaporation and the residue was purified by chromatography on a silica gel column using a 9:1 v/v mixture of dichloromethane and ethyl acetate. There was thus obtained t-butyl 4-p-dimethylaminophenyl-4-oxobut-trans-2-enoate.

EXAMPLE 10

The process described in Example 9 was repeated using the ethyl esters of the butenoic acid and the dipeptide instead of the t-butyl esters. There was thus obtained N-[3-p-dimethylaminophenyl-1-ethoxycarbonyl-3-oxopropyl]-L-alanyl-L-proline ethyl ester. This compound was separated into its two isomers by high pressure liquid chromatography using a Hichrom Hypersil OD S column with a 62:5:5 v/v/v mixture of methanol, aqueous 0.1 molar disodium hydrogen phosphate solution, and aqueous 0.1 molar sodium dihydrogen phosphate solution as eluant.

The ethyl trans-but-2-enoate was obtained by a similar process to that described in the last part of Example 9 using ethanol in place of t-butanol.

EXAMPLE 11

The process described in Example 9 was repeated using ethyl 4-p-dimethylaminophenyl-4-oxobut-trans-2-enoate and N$^6$-t-butoxycarbonyl-L-lysyl-L-proline t-butyl ester as starting materials. There were thus successively obtained N-[3-p-dimethylaminophenyl-1-ethoxycarbonyl-3-oxopropyl]-N$^6$-t-butoxycarbonyl-L-lysyl-L-proline t-butyl ester and N-[3-p-dimethylaminophenyl-1-ethoxycarbonyl-3-oxopropyl]-L-lysyl-L-proline tri-trifluoroacetate.

EXAMPLE 12

A solution of L-alanyl-L-proline t-butyl ester (0.8 g.) in dichloromethane (10 ml.) was added to a solution of t-butyl 4-(3-indolyl)-4-oxobut-trans-2-enoate (0.58 g.) in dichloromethane (20 ml.) which was protected from light, and the mixture was kept at laboratory temperature with exclusion of light for 16 hours, concentrated to a volume of 10 ml. by evaporation and kept at laboratory temperature for 24 hours. Further L-alanyl-L-proline t-butyl ester (0.75 g.) was added and the mixture was concentrated to a volume of 5 ml. by evaporation and kept at laboratory temperature for 2 days, light being excluded throughout the reaction. The mixture was then subjected to MPL chromatography on a silica gel column, using as eluant mixtures of dichloromethane and methanol initially 100:1 v/v and increasing to 100:5 v/v, and the product was finally purified by flash chromatography on a silica gel column using a 20:1 v/v mixture of dichloromethane and methanol as eluant. There was thus obtained Isomer A of N-[3-(3-indolyl)-3-oxo-1-t-butoxycarbonylpropyl]-L-alanyl-L-proline t-butyl ester.

Trifluoroacetic acid (3 ml.) was added to the above compound (0.3 g.) cooled to 0° C., and the mixture was allowed to warm up to laboratory temperature, kept at that temperature for 7 hours and then evaporated to dryness under reduced pressure, toluene being repeatedly added and removed by evaporation under reduced pressure to remove last traces of trifluoroacetic acid. There was thus obtained as an oil Isomer A of N-[1-carboxy-3-(3-indolyl)-3-oxopropyl]-L-alanyl-L-proline trifluoroacetate.

The t-butyl butenoate used as starting material was obtained as follows:

3-Bromoacetylindole (3 g.) was added to a boiling solution of (t-butoxycarbonylmethylene)triphenylphosphorane (9.5 g.) in acetonitrile (120 ml.) and the mixture was heated under reflux for 2 hours. t-Butyl bromoacetate (2.46 g.) was added and the mixture was heated under reflux for 2 hours and then evaporated to dryness under reduced pressure. The residue was purified by flash chromatography on a silica gel column using dichloromethane with increasing amounts (1%, 2% and finally 3% v/v) of methanol as eluant. The product was stirred with dichloromethane and the mixture was filtered. There was thus obtained as solid residue t-butyl 4-(3-indolyl)-4-oxobut-trans-2-enoate, which was protected from light until used as starting material.

EXAMPLE 13

The process described in Example 12 was repeated using the ethyl esters of the trans but-2-enoate and the dipeptide as starting materials (L-alanyl-L-proline ethyl ester hydrochloride and one molecular proportion of triethylamine providing one starting material). There was thus obtained, as an oil, Isomer A of N-[1-ethoxycarbonyl-3-(3-indolyl)-3-oxopropyl]-L-alanyl-L-proline ethyl ester.

When the above reaction was carried out without exclusion of light a mixture of Isomers A and B of the product was obtained.

The ethyl trans-but-2-enoate was obtained by a similar process to that described in the last part of Example 12, using (ethoxycarbonylmethylene)triphenylphosphorane in place of the t-butoxycarbonylmethylene compound, and this ester also was protected from light until used.

EXAMPLE 14

The process described in Example 12 was repeated using N$^6$-t-butoxycarbonyl-L-lysyl-L-proline t-butyl ester as starting material in place of L-alanyl-L-proline t-butyl ester. There were thus successively obtained, as oils:

Isomer A of N$^1$-[3-(3-indolyl)-3-oxo-1-t-butoxycarbonylpropyl]-N$^6$-t-butoxycarbonyl-L-lysyl-L-proline t-butyl ester, purified by MPL chromatography on a silica gel column using initially dichloromethane and finally a 40:1 v/v mixture of dichloromethane and methanol; and Isomer A of N$^1$-[1-carboxy-3-(3-indolyl)-3-oxopropyl]-L-lysyl-L-proline di-trifluoroacetate, purified by MPL chromatography using initially a 19:1 v/v mixture of dichloromethane and methanol, and finally an 11:8:4 v/v/v mixture of methanol, dichloromethane and water, as eluant.

EXAMPLE 15

The process described in Example 12 or 13 was repeated using the appropriate ethyl or t-butyl 4-heterocyclyl-4-oxobut-trans-2-enoate and either L-alanyl-L-proline t-butyl ester, or L-alanyl-L-proline ethyl ester hydrochloride together with one molecular equivalent of triethylamine to neutralise the hydrochloric acid, as starting materials. There were thus obtained the compounds described in the following table:

$$R^1COCH_2CHNHCHCON\begin{array}{c}COOR^{27}\\|\\CH_3\\|\\\\COOR^{17}\end{array}$$

| $R^1$ | $R^{27}$ | $R^{17}$ | Note |
|---|---|---|---|
| 2-furyl | t-butyl | t-butyl | |
| 2-furyl | H | H | 1 |
| 2-furyl | ethyl | ethyl | |
| 5-methylthien-2-yl | ethyl | ethyl | |
| 1-methylindol-3-yl | ethyl | ethyl | |
| 1-methylpyrrol-2-yl | ethyl | ethyl | |
| 1-methylpyrrol-2-yl | t-butyl | t-butyl | |
| 1-methylpyrrol-2-yl | H | H | 2 |
| pyrrol-2-yl | ethyl | ethyl | |
| 1,5-dimethylpyrrol-2-yl | ethyl | ethyl | |
| 2,5-dimethylpyrrol-3-yl | ethyl | ethyl | |
| 2,5-dimethylpyrrol-3-yl | ethyl | t-butyl | |
| 2,5-dimethylpyrrol-3-yl | ethyl | H | 3 |

Notes
Note 1. Product obtained as trifluoroacetate salt.
Note 2. Product purified by chromatography on Kieselgel 60 using an 11:8:2 v/v/v mixture of chloroform, methanol and water to which was added 2% by volume of aqueous ammonium hydroxide solution (specific gravity 0.91) as eluant, and isolated as a glass-like solid, m.p. 116° C. (with decomposition).
Note 3 Product purified by chromatography on Kieselgel 60 using the lower layer of a 1:1:1 v/v/v mixture of chloroform, methanol and aqueous ammonium hydroxide solution as eluant.

The butenoate starting materials were in general prepared from the appropriate haloacetylheterocycle by a similar process to that described in Example 12, or from the butenoic acid by esterification using a carbodi-imide as described in Example 9, or in the case of t-butyl esters using isobutylene as described in Example 1. Butenoic acids were obtained from the appropriate acetyl-heterocycle and glyoxylic acid as described in Example 9, or by individual procedures as described below.

4-(5-Methylthien-2-yl)-4-oxobut-trans-2-enoic acid

A solution of 2-methylthiophene (9.8 g.) in ethylene dichloride (10 ml.) was added dropwise during 90 minutes to a stirred mixture of aluminium chloride (26.4 g.), maleic anhydride (9.8 g.) and ethylene dichloride (40 ml.) at laboratory temperature, and the mixture was stirred at that temperature for 16 hours and then poured onto a mixture of crushed ice (450 g.) and concentrated aqueous hydrochloric acid (25 ml.). The mixture was extracted twice with ethyl acetate (100 ml. each time) and the combined extracts were washed with water and then with saturated sodium chloride solution, dried over magnesium sulphate and evaporated to dryness. The residue was stirred with petroleum ether (b.p. 40°-60° C.) and the mixture was filtered. There was thus obtained 4-(5-methylthien-2-yl)-4-oxobut-trans-2-enoic acid.

Ethyl 4-(1-methylindol-3-yl)-4-oxobut-trans-2-enoate was prepared by heating a mixture of the corresponding 3-indolyl ester (0.66 g.), methyl iodide (0.45 g.) and potassium carbonate (0.8 g.) under reflux in acetone solution for 24 hours, with exclusion of light, and purifying the product by chromatography on a silica gel column using dichloromethane as eluant.

The various pyrrolyl derivatives were prepared from the chloroacetylpyrroles and a phosphorane as described in Example 12, and the chloroacetylpyrroles used as intermediates were obtained as follows:

A solution of N-methylpyrrole (16.2 g.) and chloroacetonitrile (21.1 g.) in diethyl ether (100 ml.) was saturated with hydrogen chloride at 0° C., and then kept at laboratory temperature for 2 hours and filtered. The solid product was partitioned between water and diethylether (100 ml. of each) and the ethereal layer was dried and evaporated to dryness. The product was crystallised from petroleum ether (b.p. 60°-80° C.) and there was thus obtained 2-chloroacetyl-1-methylpyrrole, m.p. 46°-47° C.

Similarly obtained were 2-chloroacetylpyrrole, m.p. 116°-119° C., and 2-chloroacetyl-1,5-dimethylpyrrole, m.p. 59°-62° C.

Chloroacetyl chloride (11.3 g.) was added dropwise to a stirred solution of 2,5-dimethylpyrrole (9.5 g.) and pyridine (7.9 g.) in toluene (200 ml.) under an atmosphere of nitrogen, and the mixture was kept at laboratory temperature for 3 hours and was then poured into ice-water (200 ml.). The mixture was filtered and the solid was extracted four times with diethyl ether (200 ml. each time). The combined extracts were washed with saturated aqueous sodium chloride solution, dried and evaporated to dryness, and the residue was crystallised from acetonitrile. There was thus obtained 3-chloroacetyl-2,5-dimethylpyrrole, m.p. 149°-150° C.

EXAMPLE 16

The process described in Example 12 was repeated using $N^6$-t-butoxycarbonyl-L-lysyl-L-proline t-butyl ester and t-butyl 4-(1-methylpyrrol-2-yl)-4-oxobut-trans-2-enoate as starting materials. There were thus successively obtained, as oils:
$N^1$-[3-(1-methylpyrrol-2-yl)-3-oxo-1-t-butoxycarbonylpropyl]-$N^6$-t-butoxycarbonyl-L-lysyl-L-proline t-butyl ester, purified by chromatography on Kieselgel 60 using diethyl ether as eluant; and $N^1$-[1-carboxy-3-(1-methylpyrrol-2-yl)-3-oxopropyl]-L-lysyl-L-proline ditrifluoroacetate, purified by trituration with diethyl ether and filtration to provide the product as a solid.

EXAMPLE 17

Ethyl 6,6-ethylenedioxy-2-oxo-6-(2-thienyl)-hexanoate (3 g.) and L-alanyl-L-proline t-butyl ester (2.5 g.) were added to a suspension of freshly activated 4 Å molecular sieve (15 g.) in ethanol (35 ml.) and the mixture was stirred at laboratory temperature for 1 hour. Acetic acid (1.25 ml.) was added, and sodium cyanoborohydride (0.625 g.) was then added in portions during 1 hour. The mixture was stirred at laboratory temperature for 48 hours and then filtered, and the filtrate was evaporated to dryness under reduced pressure. The residue was purified by flash chromatography on a silica gel column using a 40:1 v/v mixture of dichloromethane and methanol as eluant. There was thus obtained as an oil N-[1-ethoxycarbonyl-5,5-ethylenedioxy-5-(2-thienyl)pentyl]-L-alanyl-L-proline t-butyl ester.

The ethyl hexanoate used as starting material was obtained as follows:

A solution of sodium cyanide (6.4 g.) in dimethyl sulphoxide (25 ml.) was heated at 100° C., 2-(3-chloropropyl)-2-(2-thienyl)-1,3-dioxolane [a known compound prepared from 2-(4-chlorobutyryl)thiophene, ethanediol and p-toluenesulphonic acid in toluene solution] was added and the mixture was heated at 100° C. for 3 hours, cooled and poured into water (300 ml.). The mixture was extracted three times with diethyl ether (100 ml. each time) and the combined extracts were washed with water, dried over magnesium sulphate and evaporated to dryness.

Methyl methylthiomethyl sulphoxide (9.85 ml.) was added slowly to a stirred suspension of sodium hydride (5.6 g. of a 50% dispersion in oil from which the oil had been removed by washing with petroleum ether b.p. 60°–80° C.) in tetrahydrofuran (80 ml.) and the mixture was stirred at laboratory temperature for 30 minutes. A solution of the 2-(3-cyanopropyl)-2-(2-thienyl)-1,3-dioxolane obtained as described in the previous paragraph (21 g.) in tetrahydrofuran (20 ml.) was added and the mixture was stirred at 60° C. for 16 hours and then cooled. Water (4 ml.) was added dropwise, and the mixture was diluted with dichloromethane (500 ml.), dried over magnesium sulphate and evaporated to dryness. The residue was purified by MPL chromatography on a silica gel column using a 50:1 v/v mixture of dichloromethane and methanol as eluant. There was thus obtained 1-[4,4-ethylenedioxy-4-(2-thienyl)butyl]-2-methylsulphinyl-2-methylthioethenamine.

Cupric chloride dihydrate (3.6 g.) and cupric oxide (6.7 g.) were added to a stirred solution of the above amine (14.5 g.) in dichloromethane (150 ml.) and the mixture was stirred at laboratory temperature for 18 hours. Further cupric chloride dihydrate (1.8 g.) and cupric oxide (3.3 g.) were added and the mixture was stirred for a further 24 hours and then filtered and the filtrate was evaporated to dryness under reduced pressure. The residue was purified by flash chromatography on a silica gel column using dichloromethane as eluant, and there was thus obtained S-methyl 6,6-ethylenedioxy-2-oxo-6-(2-thienyl)thiohexanoate.

Sodium bicarbonate (7 g.) and cupric chloride dihydrate (3.6 g.) were successively added to a stirred solution of the above thiohexanoate (6.2 g.) in ethanol (300 ml.) and the mixture was stirred at laboratory temperature for 4 hours and then evaporated to dryness under reduced pressure. Dichloromethane (300 ml.) was added, and mixture was filtered through a filter-aid and the filtrate was evaporated to dryness. The residue was purified by flash chromatography on a silica gel column using dichloromethane as eluant, and there was thus obtained as an oil ethyl 6,6-ethylenedioxy-2-oxo-6-(2-thienyl)hexanoate.

EXAMPLE 18

A solution of N-[1-ethoxycarbonyl-5,5-ethylenedioxy-5-(2-thienyl)pentyl]-L-alanyl-L-proline t-butyl ester (Example 17; 0.7 g.) in ethanol (10 ml.) which had previously been saturated with hydrogen chloride was kept at laboratory temperature for 4 days and then evaporated to dryness under reduced pressure. Aqueous N-sodium bicarbonate solution (20 ml.) was added and the mixture was extracted with dichloromethane (20 ml.). The extract was dried over magnesium sulphate and evaporated to dryness and the residue was subjected to flash chromatography on a silica gel column using a 3:2 v/v mixture of dichloromethane and ethyl acetate as eluant. There were separately and successively obtained the less polar Isomer A and the more polar Isomer B of N-[1-ethoxycarbonyl-5-oxo-5-(2-thienylpentyl]-L-alanyl-L-proline ethyl ester, the structures of which were confirmed by proton magnetic resonance and mass spectroscopy as follows:

Proton Magnetic Resonance Spectrum (in hexa-deutero-dimethyl sulphoxide at 100° C.)
-continued

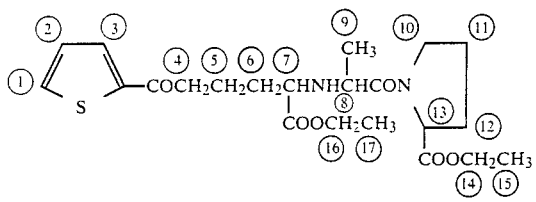

| Shift (δ) | Type of Peak | No. of H Atoms | Specific H Atoms |
|---|---|---|---|
| 7.80–7.98 | m | 2H | 1, 3 |
| 7.20 | d. of d. | 1H | 2 |
| 3.90–4.40 | m | 6H | 7 (or 8), 13, 14, 16 |
| 3.30–3.70 | m | 3H | 8 (or 7), 10 |
| 2.95 | m | 2H | 4 |
| 1.50–2.10 | m | 8H | 5, 6, 11, 12 |
| 1.05–1.35 | m | 9H | 9, 15, 17 |

| Mass Spectrum | |
|---|---|
| MASS NO | ION |
| 453 | (M + H)+ |
| 434 | M − H₂O |
| 407 | M − OC₂H₅ |
| 379 | M − COOC₂H₅ |
| 282 | M − CON(...)COOC₂H₅ |

The proton magnetic resonance and mass spectra of Isomer A were identical to those of Isomer B.

EXAMPLE 19

Aqueous N-sodium hydroxide solution (2.5 ml.) was added to a solution of N-[1-ethoxycarbonyl-5,5-ethylenedioxy-5-(2-thienyl)pentyl]-L-alanyl-L-proline t-butyl ester (Example 17; 1.2 g.) in ethanol (7.5 ml.) and the mixture was stirred at laboratory temperature for 24 hours and the ethanol was then removed by evaporation under reduced pressure. Water (10 ml.) was added, the solution was washed with dichloromethane and then acidified to pH 5 with aqueous 2N hydrochloric acid, and the mixture was filtered. There was thus obtained as solid residue Isomer A of N-[1-carboxy-5,5-ethylenedioxy-5-(2-thienyl)pentyl]-L-alanyl-L-proline t-butyl ester.

The aqueous filtrate was extracted five times with dichloromethane (10 ml. each time) and the combined extracts were dried over magnesium sulphate and evaporated to dryness. There was thus obtained as oily residue Isomer B of N-[1-carboxy-5,5-ethylenedioxy-5-(2-thienyl)pentyl]-L-alanyl-L-proline t-butyl ester.

EXAMPLE 20

A mixture of Isomer A of N-[1-carboxy-5,5-ethylenedioxy-5-(2-thienyl)pentyl]-L-alanyl-L-proline t-butyl ester (Example 19; 0.53 g.) and 90% trifluoroacetic acid (2.5 ml.) was kept at laboratory temperature for 3 hours, evaporated to dryness under reduced pressure, and toluene was repeatedly added and removed by evaporation to remove all trace of trifluoroacetic acid. There was thus obtained Isomer A of N-[1-carboxy-5-oxo-5-(2-thienyl)pentyl]-L-alanyl-L-proline as the trifluoroacetate salt.

The corresponding Isomer B was similarly obtained from Isomer B of the ethylenedioxy t-butyl ester.

EXAMPLE 21

An excess of a solution of diazomethane in diethyl ether was added to a solution of the trifluoroacetate salt of Isomer A of N-[1-carboxy-5-oxo-5-(2-thienyl)]-L-alanyl-L-proline (Example 20; 0.1 g.) in dichloromethane (50 ml.), and when the esterification was complete as shown by a persisting yellow colour of the reaction mixture the excess of diazomethane was destroyed by the addition of acetic acid. A saturated solution of hydrogen chloride in diethyl ether was added and the mixture was evaporated to dryness under reduced pressure. There was thus obtained Isomer A of N-[1-methoxycarbonyl-5-oxo-5-(2-thienyl)pentyl]-L-alanyl-L-proline methyl ester hydrochloride.

The corresponding Isomer B dimethyl ester was similarly obtained from the trifluoroacetate salt of Isomer B of the di-carboxylic acid.

EXAMPLE 22

The process described in Example 17 was repeated except that ethyl 6,6-(2,2-dimethyltrimethylene-1,3-dioxy)-2-oxo-6-(2-thienyl)hexanoate was used in place of the corresponding 6,6-ethylenedioxy compound. There was thus obtained N-[5,5-(2,2-dimethyltrimethylene-1,3-dioxy)-1-ethoxycarbonyl-5-(2-thienyl)pentyl]-L-alanyl-L-proline t-butyl ester.

The process described in Example 19 was repeated using the above compound as starting material, and there were thus obtained solid Isomer A and oily Isomer B of N-[1-carboxy-5,5-(2,2-dimethyltrimethylene-1,3-dioxy)-5-(2-thienyl)pentyl]-L-alanyl-L-proline t-butyl ester.

The process described in Example 20 was repeated using the solid Isomer A described above, and there was thus obtained the trifluoroacetate salt of Isomer A of N-[1-carboxy-5-oxo-5-(2-thienyl)pentyl]-L-alanyl-L-proline identical to that described in Example 20.

The ethyl 6,6-(2,2-dimethyltrimethylene-1,3-dioxy)-2-oxo-6-(2-thienyl)hexanoate used as starting material was obtained as follows:

A mixture of 2-(4-chlorobutyryl)thiophen (90 g.), 2,2-dimethylpropane-1,3-diol (250 g.), p-toluenesulphonic acid (10 g.) and benzene (1200 ml.) was heated under reflux for 40 hours in a Dean and Stark water-separating apparatus, cooled in an ice-bath and filtered to remove the excess of diol. Saturated aqueous sodium bicarbonate solution (100 ml.) was added, the mixture was shaken and the benzene layer was separated, dried over magnesium sulphate and evaporated to dryness under reduced pressure. The residue was purified by chromatography on a silica gel column using a 1:1 v/v mixture of hexane and dichloromethane as eluant.

A Grignard reagent was prepared during 30 minutes by conventional means from a solution of the 2-[4-chloro-1,1-(2,2-dimethyltrimethylene-1,3-dioxy)-butyl]thiophen thus obtained (7.25 g.) in tetrahydrofuran (10 ml.) and magnesium turnings (0.64 g.) under an atmosphere of argon, and the mixture was heated under reflux for 3 hours. Additional tetrahydrofuran (30 ml.) was added, and the Grignard reagent was added dropwise during 30 minutes to a stirred solution of diethyl oxalate (20.6 g.) in tetrahydrofuran (40 ml.) which was maintained at −5° C. under an atmosphere of argon. The mixture was allowed to warm up to laboratory temperature during 16 hours, quenched with saturated aqueous ammonium chloride solution and filtered. The filtrate was evaporated to dryness under reduced pressure and the residue was purified by chromatography on a silica gel column using a 3:1 v/v mixture of dichloromethane and hexane as eluant. There was thus obtained ethyl 6,6-(2,2-dimethyltrimethylene-1,3-dioxy)-2-oxo-6-(2-thienyl)hexanoate.

EXAMPLE 23

The process described in Example 17 was repeated using ethyl 2,6-dioxo-6-(2-thienyl)hexanoate as starting material in place of the corresponding 6,6-ethylenedioxy compound. The product was purified by flash chromatography as in Example 17 using a 9:1 v/v mixture of dichloromethane and ethyl acetate as eluant, and there are thus obtained as an oil N-[1-ethoxycarbonyl-5-oxo-5-(2-thienyl)pentyl]-L-alanyl-L-proline t-butyl ester.

The process described in Example 20 was repeated using the above compound as starting material, and the product was purified by chromatography on silica gel using a 3:1 v/v mixture of dichloromethane and ethanol as eluant. There was thus obtained N-[1-ethoxycarboyl-5-oxo-5-(2-thienyl)pentyl]-L-alanyl-L-proline trifluoroacetate.

The ethyl 2,6-dioxo-6-(2-thienyl)hexanoate used as starting material was obtained by shaking a solution of ethyl 6,6-(2,2-dimethyltrimethylene-1,3-dioxy)-2-oxo-6-(2-thienyl)hexanoate in ethyl acetate with aqueous 2N-hydrochloric acid, then separating the layers, washing the ethyl acetate layer with water, drying it over magnesium sulphate and evaporating it to dryness.

EXAMPLE 24

Ethyl 6,6-(2,2-dimethyltrimethylene-1,3-dioxy)-2-oxo-6-phenylhexanoate (1.67 g; prepared from 4-chlorobutyrophenone and 2,2-dimethylpropane-1,3-diol and succeeding reactions as described in Example 17) was added to a stirred mixture of ethanol (10 ml.), L-alanyl-L-proline trifluoroacetate [prepared from a solution of N-t-butoxycarbonyl-L-alanyl-L-proline (0.572 g.) in trifluoroacetic acid which was stirred at laboratory temperature for 1 hour under an atmosphere of argon and then evaporated to dryness under reduced pressure using toluene as described in Example 20] and 4 Å molecular sieve (3.4 g.), and the mixture was stirred at laboratory temperature for 30 minutes. A solution of sodium cyanoborohydride (0.192 g.) in ethanol (6 ml.) was added during 6 hours and the mixture was stirred at laboratory temperature for 10 hours, filtered through a filter-aid and the filtrate was evaporated to dryness. The residue was partitioned between saturated aqueous sodium carbonate solution and diethyl ether and the aqueous layer was separated, acidified to pH3 with aqueous 1-molar citric acid solution and extracted with dichloromethane. The extract was dried over magnesium sulphate and evaporated to dryness, and the residue was purified by chromatography on a silica gel column using a 9:1 v/v mixture of dichloromethane and methanol as eluant. There was thus obtained as an oil N-[1-ethoxycarbonyl-5,5-(2,2-dimethyltrimethylene-1,3-dioxy)-5-phenylpentyl]-L-alanyl-L-proline.

Aqueous N-sodium hydroxide solution (20 ml.) was added to a stirred solution of the above compound (0.25 g.) in ethanol (20 ml.) and the mixture was stirred at laboratory temperature for 30 minutes. Aqueous 1-molar citric acid solution (20 ml.) was added and the mixture was evaporated to dryness under reduced pressure. The residue was shaken with ethanol, the mixture was filtered and the filtrate was evaporated to dryness.

The residue was purified on a silica gel column using a 10:8 v/v/v mixture of chloroform, methanol and water as eluant, and there was thus obtained N-[1-carboxy-5,5-(2,2-dimethyltrimethylene-1,3-dioxy)-5-phenylpentyl]-L-alanyl-L-proline.

An excess of a solution of diazomethane in diethyl ether was added to a solution of the above acid (0.02 g.) in methanol (10 ml.) and the mixture was kept at laboratory temperature for 10 minutes. An excess of acetic acid was added, followed by a solution of hydrogen chloride in diethyl ether, and the mixture was evaporated to dryness under reduced pressure using toluene as described in Example 20. There was thus obtained N-[1-methoxycarbonyl-5,5-(2,2-dimethyltrimethylene-1,3-dioxy)-5-phenylpentyl]-L-alanyl-L-proline methyl ester.

EXAMPLE 25

The processes described in Examples 17 to 22 were repeated using the appropriate ethyl ω-aryl-ω,ω-dioxy-2-oxoalkanoate and the apropriate L-alanyl-L-proline derivative as starting materials. There were thus obtained the compounds described in the following tables. In the columns headed X
$X^1$ is the group

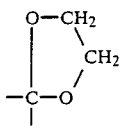

and
$X^2$ is the group

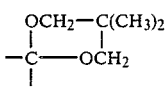

TABLE 1

$$R^1-X-(CH_2)_3-\underset{\underset{CH_3}{|}}{\overset{\overset{COOR^{27}}{|}}{CH}}-NHCH-CON\diagdown COOR^{17}$$

| $R^1$ | X | $R^{27}$ | $R^{17}$ | As Example | Note |
|---|---|---|---|---|---|
| phenyl | $-X^1-$ | ethyl | t-butyl | 17 | |
| phenyl | $-X^1-$ | H | t-butyl | 19 | |
| phenyl | $-CO-$ | H | H | 20 | 1 |
| phenyl | $-CO-$ | methyl | methyl | 21 | 2 |
| phenyl | $-X^1-$ | ethyl | H | 17 | 3 |
| phenyl | $-CO-$ | ethyl | H | 20 | 1 |
| 4-methyl-1-naphthyl | $-X^2-$ | ethyl | t-butyl | 17 | |
| 4-methyl-1-naphthyl | $-X^2-$ | H | t-butyl | 19 | |
| 4-methyl-1-naphthyl | $-CO-$ | H | H | 20 | 1 |
| 4-methyl-1-naphthyl | $-CO-$ | methyl | methyl | 21 | 2 |
| 4-methyl-1-naphthyl | $-CO-$ | ethyl | H | 20 | 1, 4 |
| 4-fluoro-1-naphthyl | $-X^2-$ | ethyl | t-butyl | 17 | |
| 4-fluoro-1-naphthyl | $-X^2-$ | H | t-butyl | 19 | |
| 4-fluoro-1-naphthyl | $-CO-$ | H | H | 20 | 1 |
| 4-fluoro-1-naphthyl | $-CO-$ | methyl | methyl | 21 | 2 |
| 4-fluoro-1-naphthyl | $-CO-$ | ethyl | H | 20 | 1, 4 |
| 4-bromo-1-naphthyl | $-X^2-$ | ethyl | t-butyl | 17 | |
| 4-bromo-1-naphthyl | $-X^2-$ | H | t-butyl | 19 | |
| 4-bromo-1-naphthyl | $-CO-$ | H | H | 20 | 1 |
| 4-bromo-1-naphthyl | $-CO-$ | methyl | methyl | 21 | 2 |
| 4-bromo-1-naphthyl | $-CO-$ | ethyl | H | 20 | 1, 4 |
| 4-methoxy-1-naphthyl | $-X^2-$ | ethyl | t-butyl | 17 | |
| 4-methoxy-1-naphthyl | $-X^2-$ | H | t-butyl | 19 | |
| 4-methoxy-1-naphthyl | $-CO-$ | H | H | 20 | 1 |
| 4-methoxy-1-naphthyl | $-CO-$ | methyl | methyl | 21 | 2 |
| 4-methoxy-1-naphthyl | $-CO-$ | ethyl | H | 20 | 1, 4 |
| 5-chloro-2-thienyl | $-X^2-$ | ethyl | t-butyl | 17 | |
| 5-chloro-2-thienyl | $-X^2-$ | H | t-butyl | 19 | |
| 5-chloro-2-thienyl | $-CO-$ | H | H | 20 | 1 |
| 5-chloro-2-thienyl | $-CO-$ | methyl | methyl | 21 | 2 |
| 5-chloro-2-thienyl | $-CO-$ | ethyl | H | 20 | 1, 4 |
| 5-methyl-2-thienyl | $-X^2-$ | ethyl | t-butyl | 17 | |
| 5-methyl-2-thienyl | $-X^2-$ | H | t-butyl | 19 | |
| 5-methyl-2-thienyl | $-CO-$ | H | H | 20 | 1 |
| 5-methyl-2-thienyl | $-CO-$ | methyl | methyl | 21 | 2 |
| 5-methyl-2-thienyl | $-CO-$ | methyl | H | 20 | 1, 4 |
| 2-furyl | $-X^1-$ | ethyl | t-butyl | 17 | |
| 2-furyl | $-X^1-$ | H | t-butyl | 19 | 6 |
| 2-furyl | $-CO-$ | H | H | 20 | 1, 7 |
| 2-furyl | $-CO-$ | ethyl | ethyl | 20/21 | 4, 8 |
| 3-thienyl | $-X^1-$ | ethyl | t-butyl | 17 | |
| 3-thienyl | $-X^1-$ | H | t-butyl | 19 | |
| 3-thienyl | $-CO-$ | H | H | 20 | 1, 7 |
| 3-thienyl | $-CO-$ | ethyl | ethyl | 20/21 | 4, 8 |
| 4-biphenylyl | $-X^2-$ | ethyl | t-butyl | 17 | 5 |
| 4-biphenylyl | $-X^2-$ | H | t-butyl | 19 | |
| 4-biphenylyl | $-CO-$ | H | H | 20 | 1 |
| 4-biphenylyl | $-CO-$ | methyl | methyl | 21 | 2 |
| benzo[b]thien-3-yl | $-X^2$ | ethyl | t-butyl | 17 | |
| benzo[b]thien-3-yl | $-X^2-$ | H | t-butyl | 19 | |
| benzo[b]thien-3-yl | $-CO-$ | H | H | 20 | 1 |
| benzo[b]thien-3-yl | $-CO-$ | methyl | methyl | 21 | 2 |
| 3-pyridyl | $-X^1-$ | ethyl | t-butyl | 17 | |
| 3-pyridyl | $-CO-$ | ethyl | ethyl | 18 | |
| 3-pyridyl | $-X^1-$ | H | t-butyl | 19 | |
| 3-pyridyl | $-CO-$ | H | H | 20 | 1, 7 |

TABLE 2

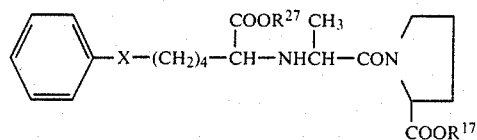

| X | $R^{27}$ | $R^{17}$ | As Example | Note |
|---|---|---|---|---|
| $-X^1-$ | ethyl | t-butyl | 17 | |
| $-X^1-$ | H | t-butyl | 19 | |
| —CO— | H | H | 20 | 1 |
| —CO— | methyl | methyl | 21 | 2 |

TABLE 3

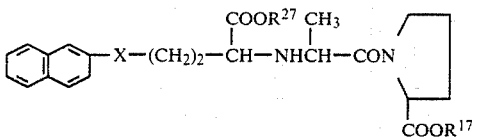

| X | $R^{27}$ | $R^{17}$ | As Example | Note |
|---|---|---|---|---|
| $-X^2-$ | ethyl | t-butyl | 22 | |
| $-X^2-$ | H | t-butyl | 19 | 6 |
| —CO— | H | H | 20 | 1 |
| —CO— | ethyl | ethyl | 20/21 | 4, 8 |

Notes
1 Product isolated as trifluoroacetate salt.
2 Reaction with diazomethane carried out in methanol solution.
3 L-alanyl-L-proline used as starting material.
4 Initial dioxy, ethyl ester, t-butyl ester reacted with trifluoroacetic acid.
5 Starting material prepared as in Example 22 (see below).
6 Hydrolysis of ethyl ester carried out in methanol solution.
7 Product purified by chromatography on Sephadex LH 20 using methanol as eluant.
8 Proline ethyl ester formed by using diazoethane in methanol solution.

PREPARATION OF STARTING MATERIALS

The ethyl 2-oxoalkanoate starting materials were in general prepared as described in Example 17 or 22 from the appropriate ω-chloroalkanoyl-aryl compound (prepared by a Friedel-Crafts reaction of the aromatic compound and the ω-chloroalkanoyl chloride in the presence of aluminium chloride) and the appropriate diol, followed by the series of reactions described in Example 17 or, as indicated by Note 5, in Example 22.

The Friedel-Crafts reaction is exemplified by the following preparation of 4-chloro-1-(2-furyl)butan-1-one:

4-Chlorobutyryl chloride (28.2 g.) was added to a stirred suspension of aluminium chloride (26.6 g.) in carbon disulphide (250 ml.) which was maintained under an atmosphere of nitrogen, and the mixture was stirred at laboratory temperature for 30 minutes and then cooled to 0° C. A solution of furan (13.6 g.) in carbon disulphide (50 ml.) was added during 30 minutes to the stirred, cooled solution, and then ice-cold water (250 ml.) was added. The liquid was decanted off and the solid residue was vigorously stirred with ice-cold water (100 ml.) and diethyl ether (100 ml.). The mixture was filtered and the solid residue was extracted twice with diethyl ether (100 ml. each time). The two biphasic liquid solutions were separated and the combined aqueous layers were extracted twice with diethyl ether (100 ml. each time). All the organic solutions and extracts were combined, washed twice with saturated aqueous sodium bicarbonate solution (50 ml. each time) and twice with saturated sodium chloride solution (50 ml. each time), dried over sodium sulphate and evaporated to dryness. The residue was flash chromatographed on a silica gel column (200 g.) using a 50:1 v/v mixture of toluene and ethyl acetate as eluant. The product which was eluted was dissolved in diethyl ether (100 ml.) and the solution was washed four times with aqueous 0.5M-sodium carbonate solution (25 ml. each time), once with saturated aqueous sodium chloride solution, dried over sodium sulphate and evaporated to dryness. The residue was distilled over a short path at 0.5 mm.Hg. pressure, bath temperature 95° C., and there was thus obtained 4-chloro-1-(2-furyl)butan-1-one.

Alternatively, the Friedel-Crafts reaction may be carried out using an ω-cyanoalkanoylchloride, and the ω-cyanoalkanoyl-aryl compound thus obtained then reacted with the appropriate diol, thereby avoiding the cyanide step described in the second paragraph of Example 17.

Yet alternatively the -cyanoalkanoyl-aryl compound may be obtained by the process exemplified by the following preparation of 4-cyano-1-(3-thienyl)butan-1-one:

Thiophene-3-carboxaldehyde (8.96 g.) was added dropwise during 5 minutes to a stirred mixture of trimethylsilyl cyanide (7.92 g.) and zinc iodide (0.001 g.) which was kept at laboratory temperature by cooling with a water bath, and the mixture was stirred at laboratory temperature for 2 hours and then distilled over a short path at 0.1 mm. Hg. pressure, bath temperature 100° C.

A solution of the 2-(3-thienyl)-2-trimethylsilyloxyacetonitrile thus obtained (14.0 g.) in tetrahydrofuran (12 ml.) was added to a stirred solution of lithium diisopropylamide [prepared at 0° C. in tetrahydrofuran solution (200 ml.) from diisopropylamine (6.7 g.) and n-butyl-lithium (43.4 ml. of 1.55 molar solution in hexane)] in tetrahydrofuran (200 ml.) which was cooled to −78° C. under an atmosphere of nitrogen, and the mixture was stirred at that temperature for 15 minutes. 4-Bromobutyronitrile (9.8 g.) was added and the mixture was stirred at −78° C. for 1 hour and then at laboratory temperature for 1 hour. Aqueous N-hydrochloric acid (75 ml.) was added, the mixture was stirred at laboratory temperature for 90 minutes and the phases were then separated. The aqueous phase was extracted twice with ethyl acetate (100 ml. each time) and the combined organic phase and extract were stirred with aqueous N-sodium hydroxide solution (50 ml.) for 18 hours. The organic phase was separated, dried and evaporated to dryness and the residue was flash chromatographed on a silica gel column using a 19:1 v/v mixture of toluene and ethyl acetate as eluant. There was thus obtained as an oil 4-cyano-1-(3-thienyl)butan-1-one.

Some of the novel intermediates used were solids characterised by melting point as follows:

| | |
|---|---|
| 4-cyano-1-phenylbutan-1-one | 38–40° C. |
| 4-cyano-1-(2-furyl)butan-1-one | 25–27° C. |
| 5,5-ethylenedioxy-5-phenylpentanonitrile | 47–48.5° C. |
| ethyl 6,6-ethylenedioxy-2-oxo-6-(3-thienyl)-hexanoate | 51–52° C. |
| 4-chloro-1-(4-biphenylyl)butan-1-one | 119–120° C. |
| ethyl 6,6-ethylenedioxy-2-oxo-6-(3-pyridyl)hexanoate | 35–37° C. |
| 5,5-ethylenedioxy-5-(3-thienyl)pentanonitrile | 34–36° C. |

EXAMPLE 26

The process described in Example 17 was repeated using ethyl 6-benzo[b]fur-2-yl-6,6-(2,2-dimethyltrimethylene-1,3-dioxy)-2-oxohexanoate as starting material in place of the corresponding 2-thienyl derivative. The product was purified by chromatography on a silica gel column using a 1:1 v/v mixture of ethyl acetate and petroleum ether (b.p. 60°–80° C.) as eluant and there were thus obtained separately, as oils, Isomer A and Isomer B of N-[5-(benzo[b]fur-2-yl)-5,5-(2,2-dimethyltrimethylene-1,3-dioxy)-1-ethoxycarboxylpentyl]-L-alanyl-L-proline t-butyl ester.

Each isomer separately was hydrolysed to the corresponding 1-carboxy-derivative by the process described in Example 19, and each of these carboxy derivatives was separately hydrolysed by the process described in Example 20 to give, as oils, Isomer A and Isomer B of N-[5-(benzo[b]fur-2-yl)-1-carboxy-5-oxopentyl]-L-alanyl-L-proline trifluoroacetate.

Each of the above acids was separately reacted in methanol solution with ethereal diazomethane by a similar process to that described in the last part of Example 24, and there were thus obtained Isomer A and Isomer B of N-[5-(benzo[b]fur-2-yl)-1-methoxycarbonyl-5-oxopentyl]-L-alanyl-L-proline methyl ester.

The ethyl hexanoate used as starting material was obtained from benzo[b]furan-2-carboxaldehyde by reaction with trimethylsilyl cyanide, lithium diisopropylamide and 4-bromobutyronitrile by a similar process to that described in the penultimate paragraph of Example 25 to give 1-(benzo[b]fur-2-yl)-4-cyanobutan-1-one, m.p. 79° C., which was then converted to the ethyl hexanoate by a similar process to that described in Example 17.

Benzo[b]furan-2-carboxaldehyde itself was obtained as follows:

A mixture of salicylaldehyde (122 g.), 2,2-diethoxyethyl bromide (216 g.), potassium carbonate (152 g.) and dimethylformamide (500 ml.) was heated under reflux for 90 minutes, cooled and filtered and the filtrate was evaporated to dryness under reduced pressure. The residue was partitioned between ethyl acetate and water and the organic layer was dried and evaporated to dryness. The residue was distilled under reduced pressure and there was thus obtained 2-(2,2-diethoxyethoxy)benzaldehyde, b.p. 135°–138° C./0.4 mm.Hg.

A solution of the above compound (168 g.) in acetic acid (420 ml.) was heated under reflux for 20 hours, the acetic acid was removed by evaporation under reduced pressure and the residue was distilled under reduced pressure. There was thus obtained benzo[b]furan-2-carboxaldehyde, b.p. 92°–95° C./0.5 mm.Hg.

EXAMPLE 27

The process described in Example 17 was repeated using the appropriate dipeptide derivative in place of L-alanyl-L-proline t-butyl ester. There were thus obtained as oils the compounds described in the following tables. In the column headed X, $X^1$ and $X^2$ are as in Example 25. BOC in $R^4$ represents t-butoxycarbonyl.

TABLE 1

$$\underset{S}{\boxed{\phantom{xx}}}-X-(CH_2)_3\underset{|}{C}HNHCHR^4CONR^5CHR^6COOR^{17}$$
$$\phantom{xxxxxxxxxxxxxxxxxxxx}COOR^{27}$$

| Compound | X | $R^{27}$ | $R^4$ | $R^5$ | $R^6$ | $R^{17}$ | Note |
|---|---|---|---|---|---|---|---|
| 1 | —$X^2$— | ethyl | H | | —(CH$_2$)$_3$ | H | 1 |
| 2 | —CO— | ethyl | H | | —(CH$_2$)$_3$ | H | 2 |
| 3 | —CO— | H | H | | —(CH$_2$)$_3$ | H | 3 |
| 4 | —$X^2$— | ethyl | —(CH$_2$)$_4$NH(BOC) | | —(CH$_2$)$_3$ | t-butyl | 4 |
| 5 | —$X^2$— | H | —(CH$_2$)$_4$NH(BOC) | | —(CH$_2$)$_3$ | t-butyl | 5 |
| 6 | —CO— | H | —(CH$_2$)$_4$NH$_2$ | | —(CH$_2$)$_3$ | H | 6 |
| 7 | —$X^2$— | ethyl | methyl | | —CH$_2$SCH$_2$— | H | 7 |
| 8 | —CO— | ethyl | methyl | | —CH$_2$SCH$_2$— | H | 8 |
| 9 | —CO— | H | methyl | | —CH$_2$SCH$_2$— | H | 9 |
| 10 | —$X^2$— | ethyl | H | H | 3-indolylmethyl | H | 10 |
| 11 | —CO— | H | H | H | 3-indolylmethyl | H | 11 |
| 12 | —$X^2$— | ethyl | isopropyl | H | 3-indolylmethyl | H | 12 |
| 13 | —CO— | ethyl | isopropyl | H | 3-indolylmethyl | H | 13 |
| 14 | —CO— | H | isopropyl | H | 3-indolylmethyl | H | 14 |
| 15 | —CO— | ethyl | methyl | isopropyl | H | ethyl | 15 |

Notes
1 Glycyl-L-proline used as starting material.
Product purified by chromatography on silica gel using
9:1 v/v dichloromethane/methanol.
2 The hydrolysis of the —$X^2$— group of Compound
1 was carried out as follows:-
Aqueous N—hydrochloric acid (10 ml.) was added
to a solution of Compound 1 (0.87 g.) in tetrahydrofuran
(30 ml.) and the mixture was kept at laboratory
temperature for 2 hours and then evaporated to dryness
under reduced pressure. The residue was purified by
elution of the hydrochloride salt thus obtained from a
silica gel column using a 19:1 v/v mixture of
dichloromethane and methanol as eluant.
3 Hydrolysis of Compound 2 with sodium hydroxide
in methanol solution. Product purified by elution of
hydrochloride salt from a Sephadex column with methanol.

TABLE 1-continued

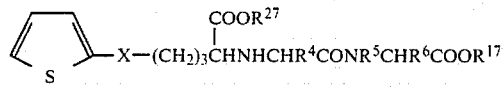

| Compound | X | R²⁷ | R⁴ | R⁵ | R⁶ | R¹⁷ | Note |
|---|---|---|---|---|---|---|---|

4 N⁶—t-Butoxycarbonyl-L-lysyl-L-proline t-butyl ester used as starting material.
5 Compound 4 hydrolysed by process described in Example 19.
6 Compound 5 hydrolysed by process described in Example 20. Product isolated as di-trifluoroacetate.
7 N—(L-Alanyl)thiazolidine-4-(R)-carboxylic acid used as starting material.
8 Compound 7 hydrolysed as under Note 2. Product purified by chromatography on silica gel using 9:1 v/v dichloromethane/methanol.
9 Compound 8 hydrolysed and purified as under Note 3. Product isolated as hydrochloride salt.
10 Glycyl-L-tryptophan used as starting material. Product isolated as under Note 1.
11 Compound 11 treated initially as under Note 3 and then as under Note 2 without isolation of intermediate. Product purified by elution of hydrochloride salt from a Sephadex column with methanol.
12 L-Valyl-L-tryptophan used as starting material
13 Compound 12 hydrolysed as under Note 2. Product purified by chromatography of hydrochloride salt on silica gel using 19:1 v/v dichloromethane/methanol.
14 Compound 13 hydrolysed and purified as under Note 3. Product isolated as hydrochloride salt.
15 L-Alanyl-N—isopropylglycine ethyl ester used as starting material.

TABLE 2

$$\underset{S}{\text{thienyl}}-X-(CH_2)_3\underset{|}{\overset{COOR^{27}}{C}H}-NH-\underset{|}{\overset{(CH_2)_4NHR}{C}H}-CON\underset{COOR^{17}}{\diagdown}$$

| Compound No. | X | R²⁷ | R | R¹⁷ | Note |
|---|---|---|---|---|---|
| 16 | —X¹— | ethyl | BOC | t-butyl | 4, 16 |
| 17 | —CO— | ethyl | H | ethyl | 17 |
| 18 | —X¹— | H | BOC | t-butyl | 18 |
| 19 | —CO— | H | H | H | 19 |
| 20 | —CO— | ethyl | H | H | 20 |

Notes
16 Product purified by chromatography on silica gel using 5:3 v/v toluene/ethyl acetate. Some separation of isomers achieved.
17 Compound 16 reacted with ethanol/hydrogen chloride as in Example 18. Product purified by chromatography on silica gel using 16:4:0.1 v/v/v chloroform/methanol/triethylamine.
18 Compound 17 hydrolysed by process described in Example 19.
19 Compound 18 hydrolysed by process described in Example 20. Product purified by elution of trifluoroacetate salt from a Sephadex column with methanol.
20 Compound 16 hydrolysed by process decribed in Example 20. Product purified as under Note 19.

Some of the compounds described above were converted to methyl esters by the process described in Example 21. There were thus obtained the following compounds:

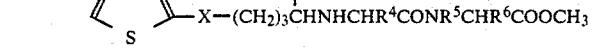

| X | R²⁷ | R⁴ | R⁵ | R⁶ | From Compound No. |
|---|---|---|---|---|---|
| X² | ethyl | H |  | —(CH₂)₃— | 1 |
| CO | ethyl | H |  | —(CH₂)₃— | 2 |
| CO | methyl | H |  | —(CH₂)₃— | 3 |
| CO | ethyl | methyl |  | —CH₂SCH₂— | 8 |
| CO | methyl | methyl |  | —CH₂SCH₂— | 9 |
| X² | ethyl | H | H | 3-indolyl methyl | 10 |
| CO | methyl | H | H | 3-indolyl-methyl | 11 |
| CO | ethyl | isopropyl | H | 3-indolyl-methyl | 13 |
| CO | methyl | isopropyl | H | 3-indolyl-methyl | 14 |

EXAMPLE 28

The process described in Example 17 was repeated except that ethyl 6,6-(2,2-dimethyltrimethylene-1,3-dioxy)-2-oxo-6-(2-thienyl)hexanoate and L-glutamyl-L-proline di-t-butyl ester were used as starting materials. There was thus obtained as an oil N-[5,5-(2,2-dimethyl-trimethylene-1,3-dioxy)-1-ethoxycarbonyl-5-(2-thienyl)pentyl]-L-glutamyl-L-proline di-t-butyl ester.

The process described in Example 19 was repeated using the above compound as starting material. There was thus obtained as a solid N-[1-carboxy-5,5-(dimethyltrimethylene-1,3-dioxy)-5-(2-thienyl)pentyl]-L-glutamyl-L-proline di-t-butyl ester which was purified by flash chromatography on a silica gel column using a 100:13 v/v mixture of ethyl acetate and methanol as eluant.

The process described in Example 20 was repeated using the above compound as starting material. There was thus obtained as a solid N-[1-carboxy-5-oxo-5-(2-thienyl)pentyl]-L-glutamyl-L-proline trifluoroacetate.

The process described in Example 20 was repeated using the compound prepared according to the first paragraph above as starting material. There was thus obtained N-[1-ethoxycarbonyl-5-oxo-5-(2-thienyl)pentyl]-L-glutamyl-L-proline trifluoroacetate.

The process described in Example 18 was repeated using the compound prepared according to the first paragraph above as starting material. There was thus obtained N-[1-ethoxycarbonyl-5-oxo-5-(2-thienyl)pentyl]-L-glutamyl-L-proline diethyl ester.

The process described in Example 21 was repeated using the tri-acid trifluoroacetate salt described in the third paragraph above as starting material. There was thus obtained N-[1-methoxycarbonyl-5-oxo-5-(2-thienyl)pentyl]-L-glutamyl-L-proline dimethyl ester.

EXAMPLE 29

The process described in Example 17 was repeated using ethyl 5,5-ethylenedioxy-2-oxo-5-phenylpentanoate and L-alanyl-L-proline as starting materials. There was thus obtained as an oil N-[1-ethoxycarbonyl-4,4-ethylenedioxy-4-phenylbutyl]-L-alanyl-L-proline.

Trifluoroacetic acid (0.25 ml.) was added to a stirred solution of the above compound (0.448 g.) in dichloromethane (2 ml.) and the mixture was stirred at laboratory temperature for 2 hours and then evaporated to dryness using toluene as described in Example 20. The residue was purified by preparative plate chromatography on silica gel using a 3:1 v/v mixture of dichloromethane and methanol as eluant, and there was thus obtained as an oil N-[1-ethoxycarbonyl-4-oxo-4-phenylbutyl]-L-alanyl-L-proline trifluoroacetate.

The ethyl pentanoate used as starting material was prepared from the known 2-(2-cyanoethyl)-2-phenyl-1,3-dioxolane by a similar process to that described in the last three paragraphs of Example 17.

EXAMPLE 30

The process described in Example 29 was repeated except that L-alanyl-L-proline t-butyl ester was used as starting material in place of the free dipeptide. There was thus obtained as an oil N-[1-ethoxycarbonyl-4,4-ethylenedioxy-4-phenylbutyl]-L-alanyl-L-proline t-butyl ester.

Aqueous N-sodium hydroxide solution (2.4 ml.) was added to a stirred solution of the above compound (1.1 g.) in ethanol (5 ml.) and the mixture was stirred at laboratory temperature for 4 hours, diluted with water (10 ml.) and the ethanol was removed by evaporation under reduced pressure. The residue was acidified to pH6 with aqueous N-hydrochloric acid and the mixture was extracted twice with dichloromethane. The combined extracts were dried over magnesium sulphate and evaporated to dryness and there was thus obtained as oily residue N-[1-carboxy-4,4-ethylenedioxy-4-phenylbutyl]-L-alanyl-L-proline t-butyl ester.

The process described in Example 20 was repeated using the above compound as starting material. There was thus obtained N-[1-carboxy-4-oxo-4-phenylbutyl]-L-alanyl-L-proline.

A solution of the above compound (0.2 g.) in methanol (5 ml.) was added to a stirred solution of thionyl chloride (1.0 ml.) in methanol (5 ml.) which was maintained at 0° C., and the mixture was stirred at that temperature for 30 minutes and then at laboratory temperature for 3 hours, and then evaporated to dryness under reduced pressure, using toluene as described in Example 20 to remove last traces of thionyl chloride. The residue was purified by chromatography on a silica gel column using a 49:1 v/v mixture of dichloromethane and methanol, and then a 9:1 mixture of dichloromethane and methanol, as eluants. There was thus obtained as an oil N-[1-methoxycarbonyl-4-oxo-4-phenylbutyl]-L-alanyl-L-proline methyl ester.

EXAMPLE 31

A mixture of N-(dimethoxycarbonylmethyl)-L-alanyl-L-proline t-butyl ester (2.0 g.), 3-dimethylamino-1-(2-thienyl)propan-1-one hydrochloride (1.8 g.), potassium carbonate (2.0 g.) and methanol (15 ml.) was stirred at laboratory temperature for 16 hours and then evaporated to dryness under reduced pressure. The residue was stirred with dichloromethane, the mixture was filtered through a filter-aid and the filtrate was evaporated to dryness under reduced pressure. The residue was purified by chromatography on a silica gel column using a 19:1 v/v mixture of dichloromethane and ethyl acetate as eluant. There was thus obtained as an oil N-[1,1-dimethoxycarbonyl-4-oxo-4-(2-thienyl)butyl]-L-alanyl-L-proline t-butyl ester.

The N-(dimethoxycarbonylmethyl)-L-alanyl-L-proline t-butyl ester used as starting material was obtained as follows:

Dimethyl bromomalonate (6.6 ml.) was added to a stirred solution of L-alanyl-L-proline t-butyl ester (22.9 g.) in dichloromethane (40 ml.) which was cooled to 0° C., and the mixture was allowed to warm up to laboratory temperature and stirred at that temperature for 16 hours, then diluted with dichloromethane (150 ml.). The solution was washed successively twice with aqueous 0.5N-citric acid solution (150 ml. each time), water (200 ml.) and saturated aqueous sodium chloride solution (200 ml.), dried over magnesium sulphate and evaporated to dryness. The residue was purified by chromatography on a silica gel column using a 4:1 v/v mixture of dichloromethane and ethyl acetate as eluant, and there was thus obtained as an oil N-(dimethoxycarbonylmethyl)-L-alanyl-L-proline t-butyl ester.

EXAMPLE 32

Aqueous N-sodium hydroxide solution (6.2 ml.) was added to a solution of N-[1,1-dimethoxycarbonyl-4-oxo-4-(2-thienyl)butyl]-L-alanyl-L-proline t-butyl ester (Example 31; 3.0 g.) in a mixture of methanol (3 ml.) and water (1.5 ml.) and the mixture was stirred at laboratory temperature for 16 hours and then evaporated to dryness under reduced pressure. The mixture was partitioned between water and ethyl acetate and the aqueous layer was separated, acidified to pH 5 with aqueous N-hydrochloric acid and extracted with dichloromethane. The extract was dried over magnesium sulphate and evaporated to dryness. There was thus obtained as residual oil N-[1-methoxycarbonyl-4-oxo-4-(2-thienyl)butyl]-L-alanyl-L-proline t-butyl ester.

A mixture of the above compound (2.0 g.) and trifluoroacetic acid (30 ml.) was kept at laboratory temperature for 4 hours and then evaporated to dryness under reduced pressure. The residue was purified by chromatography on a silica gel column using a 9:1 v/v mixture of dichloromethane and ethanol as eluant. There was thus obtained as an oil N-[1-methoxycarbonyl-4-oxo-4-(2-thienyl)butyl]-L-alanyl-L-proline trifluoroacetate.

EXAMPLE 33

Aqueous N-sodium hydroxide solution (4.7 ml.) was added to a solution of N-[1-methoxycarbonyl-4-oxo-4-(2-thienyl)butyl]-L-alanyl-L-proline t-butyl ester (Example 32; 2.0 g.) in a mixture of methanol (3 ml.) and water (1.5 ml.) and the mixture was stirred at laboratory temperature for 16 hours and then evaporated to dryness under reduced pressure. The residue was partitioned between water and ethyl acetate and the aqueous layer was separated, acidified to pH 5 with aqueous N-hydrochloric acid and extracted with dichloromethane. The extract was dried over magnesium sulphate and evaporated to dryness, and there was thus obtained as an oil N-[1-carboxy-4-oxo-4-(2-thienyl)butyl]-L-alanyl-L-proline t-butyl ester.

The above compound was treated with trifluoroacetic acid as described in the last paragraph of Example 32 and there was thus obtained as an oil N-[1-carboxy-4-oxo-4-(2-thienyl)butyl]-L-alanyl-L-proline trifluoroacetate.

EXAMPLE 34

A mixture of N-[1,1-dimethoxycarbonyl-4-oxo-4-(2-thienyl)butyl]-L-alanyl-L-proline t-butyl ester (Example 31; 1.5 g.) and trifluoroacetic acid (20 ml.) was kept at laboratory temperature for 2 hours and then evaporated to dryness under reduced pressure at less than 30° C., using toluene as described in Example 20. There was thus obtained as an oil N-[1,1-dimethoxycarbonyl-4-oxo-4-(2-thienyl)butyl]-L-alanyl-L-proline trifluoroacetate.

EXAMPLE 35

Sodium hydride (0.144 g.) was added to a solution of N-[di-t-butoxycarbonylmethyl]-L-alanyl-L-proline t-butyl ester (1.44 g.) in tetrahydrofuran (40 ml.), the mixture was stirred at laboratory temperature for 5 minutes and N-[3-(3-indolyl)-3-oxopropyl]trimethylammonium iodide (1.0 g.) was then added. The mixture was stirred at laboratory temperature for 3 hours, water (0.5 ml.) was added and the mixture was evaporated to dryness under reduced pressure. The residue was purified by chromatography on a silica gel column using a 99:1 v/v mixture of dichloromethane and methanol as eluant. There was thus obtained N-[4-(3-indolyl)-4-oxo-1,1-di-t-butoxycarbonylbutyl]-L-alanyl-L-proline t-butyl ester.

The above compound was treated with trifluoroacetic acid as described in Example 34, and there was thus obtained as an oil N-[1-carboxy-4-(3-indolyl)-4-oxobutyl]-L-alanyl-L-proline.

The N-[di-t-butoxycarbonylmethyl]-L-alanyl-L-proline t-butyl ester used as starting material was obtained as follows:

Di-t-butyl bromomalonate (15.9 g.) was added to a stirred solution of L-alanyl-L-proline t-butyl ester (26 g.) in toluene (30 ml.) which was cooled to 0° C., and the mixture was allowed to warm up to laboratory temperature during 2 hours and was stirred at that temperature for 14 hours. Diethyl ether (300 ml.) was added, the mixture was filtered to remove unreacted L-alanyl-L-proline t-butyl ester as the hydrobromide salt thereof, and the filtrate was evaporated to dryness under reduced pressure. The residue was dissolved in ethyl acetate (400 ml.) and the mixture was washed successively twice with aqueous 0.5N-citric acid solution (100 ml. each time), once with water (100 ml.) and once with saturated aqueous sodium chloride solution (100 ml.), dried over magnesium sulphate and evaporated to dryness under reduced pressure. The residue was purified by chromatography on a silica gel column using a 9:1 v/v mixture of dichloromethane and ethyl acetate as eluant, and there was thus obtained as an oil N-[di-t-butoxycarbonylmethyl]-L-alanyl-L-proline t-butyl ester.

EXAMPLE 36

A solution of sodium ethoxide in ethanol was added dropwise to a stirred solution of N-(diethoxycarbonylmethyl)-L-alanyl-L-proline t-butyl ester (1.0 g.), β-chloropropiophenone (0.42 g.) and potassium acetate (0.36 g.) in ethanol (10 ml.) until the mixture was just basic, and the mixture was stirred at laboratory temperature for 16 hours. Acetic acid was added until the pH of the mixture was 6, and the mixture was evaporated to dryness under reduced pressure. Trifluoroacetic acid (20 ml.) was added and the mixture was kept at laboratory temperature for 1 hour and then evaporated to dryness using toluene as described in Example 20. There was thus obtained as an oil N-[1,1-diethoxycarbonyl-4-oxo-4-phenylbutyl]-L-alanyl-L-proline trifluoroacetate.

The N-(diethoxycarbonylmethyl)-L-alanyl-L-proline t-butyl ester used as starting material was obtained from diethyl bromomalonate (9.56 g.), L-alanyl-L-proline t-butyl ester (10.0 g.) and triethylamine (5.5 ml.) in dichloromethane (50 ml.) by a similar process to that described in Example 31 for the preparation of the corresponding dimethoxycarbonyl analogue. It was purified by chromatography on silica gel using a 9:1 v/v mixture of dichloromethane and ethyl acetate as eluant.

EXAMPLE 37

The process described in Examples 31, 32, 34 and 35 were repeated using the appropriate 3-dimethylamino-1-arylpropan-1-one hydrochloride (Note 1), N-(3-aryl-3-oxopropyl)trimethylammonium iodide (Note 2) or β-chloropropionyl-aryl compound (Note 3) and the appropriate N-(dialkoxycarbonylmethyl)-L-aminoacyl-L-proline t-butyl ester as initial starting materials. There were thus obtained as oils the compounds shown in the following tables (BOC indicates t-butoxycarbonyl):

$$R^1COCH_2CH_2\underset{\underset{COOR^{27}}{|}}{\overset{\overset{COOR^{27}}{|}}{C}}NHCHR^4CON\diagup\diagdown COOR^{17}$$

| $R^1$ | $R^4$ | $R^{27}$ | $R^{17}$ | As Process | Note |
|---|---|---|---|---|---|
| 2-furyl | methyl | methyl | t-butyl | 31 | 1 |
| 2-furyl | methyl | methyl | H | 34 | 4 |
| 2-furyl | methyl | t-butyl | t-butyl | 35 | 1 |
| 3-pyridyl | methyl | t-butyl | t-butyl | 35 | 1 |
| benzo[b]-fur-2-yl | methyl | t-butyl | t-butyl | 31 | 2, 5 |
| 4-biphenylyl | methyl | methyl | t-butyl | 31 | 1, 7 |
| benzo[b]thien-3-yl | methyl | methyl | t-butyl | 31 | 3 |
| 2-thienyl | —(CH$_2$)$_4$NH(BOC) | methyl | t-butyl | 31 | 1 |
| 2-thienyl | —(CH$_2$)$_4$NH(BOC) | t-butyl | t-butyl | 31 | 1, 11 |

-continued

| | | | | | |
|---|---|---|---|---|---|
| benzo[b]fur-2-yl | —(CH$_2$)$_4$NH(BOC) | t-butyl | t-butyl | 31 | 2 |

$$R^1COCH_2CH_2\overset{\overset{\displaystyle COOR^{27}}{|}}{C}HNHCHR^4CON\diagdown\!\!\diagup$$
$$COOR^{17}$$

| R$^1$ | R$^4$ | R$^{27}$ | R$^{17}$ | As Process | Note |
|---|---|---|---|---|---|
| 2-furyl | methyl | H | H | 34/35 | 4 |
| 3-pyridyl | methyl | H | H | 34/35 | 4 |
| benzo[b]fur-2-yl | methyl | H | H | 34 | 4, 6 |
| 4-biphenylyl | methyl | methyl | t-butyl | 32 | 8 |
| 4-biphenylyl | methyl | methyl | H | 32 | 4, 9 |
| 4-biphenylyl | methyl | H | H | 10 | |
| benzo[b]thien-3-yl | methyl | methyl | H | 32 | 4 |
| benzo[b]thien-3-yl | methyl | H | H | 10 | |
| 2-thienyl | —(CH$_2$)$_4$NHBOC | methyl | t-butyl | 32 | |
| 2-thienyl | —(CH$_2$)$_4$NH$_2$ | methyl | H | 32 | 4, 9 |
| 2-thienyl | —(CH$_2$)$_4$NH$_2$ | H | H | 34 | 12 |
| benzo[b]fur-2-yl | —(CH$_2$)$_4$NH$_2$ | H | H | 34 | 12 |

Notes 1–3
See above as to which starting material was used
Note 4
Product isolated as trifluoroacetate salt.
Note 5
Purified by chromatography on Kieselgel 60 using a 1:1 v/v mixture of ethyl acetate and petroleum ether (b.p. 60–80° C.) as eluant.
Note 6
Purified by chromatography on Kieselgel 60 using an 11:8:5 v/v/v mixture of chloroform, methanol and water as eluant.
Note 7
Purified by chromatography on silica gel using a 2:1 v/v mixture of toluene and ethyl acetate as eluant.
Note 8
Purified by chromatography on silica gel using a 19:1 v/v mixture of dichloromethane and ethanol as eluant.
Note 9
Purified by chromatography on silica gel using a 9:1 v/v mixture of dichloromethane and methanol as eluant.
Note 10
Prepared by hydrolysis of the monomethyl ester (preceding compound in table) with sodium hydroxide in aqueous methanol.
Note 11
Purified by chromatography on silica gel using a 40:1 v/v mixture of dichloromethane and methanol as eluant.
Note 12
Product isolated as di-trifluoroacetate salt by action of trifluoroacetic acid on tetra-butoxycarbonyl compound.

The 3-dimethylamino-1-arylpropan-1-one and N-(3-aryl-3-oxopropyl)trimethylammonium iodide derivatives used as starting materials were prepared by a conventional Mannich reaction exemplified by the following:

A mixture of 2-acetylbenzo[b]furan (17.0 g.), paraformaldehyde (3.6 g.), ethanol (50 ml.) and concentrated aqueous hydrochloric acid (0.3 ml.) was heated under reflux for 2 hours, diluted with ethanol (100 ml.), cooled to 0° C. for 18 hours and then filterd. There was thus obtained 3-dimethylamino-1-(benzo[b]fur-2-yl)propan-1-one hydrochloride, m.p. 188° C.

Aqueous 2N-sodium hydroxide solution (10 ml.) was added to a stirred solution of the above hydrochloride (5.0 g.) in water (60 ml.) which was cooled to 0° C., and the mixture was immediately extracted three times with diethyl ether (25 ml. each time). The combined extracts were dried over magnesium sulphate and evaporated to dryness and the residue was dissolved in iodomethane (80 ml.). The mixture was heated under reflux for 22 hours, cooled and filtered and the solid product was crystallised from methanol. There was thus obtained N-(3-benzo[b]fur-2-yl)-3-oxopropyl]trimethylammonium iodide, m.p. 197°–198° C.

The $\beta$-chloropropionyl-aryl compounds used as starting material were prepared by a standard Friedel-Crafts reaction of the aromatic compound and 3-chloropropionyl chloride in dichloromethane solution in the presence of aluminium chloride. 3-Chloropropionyl-benzo[b]thiophene has m.p. 63°–65° C.

The N-(dimethoxycarbonylmethyl)- and N-(di-t-butoxycarbonylmethyl)-L-(N$^6$-t-butoxycarbonyl)-lysyl-L-proline t-butyl esters used as starting materials were prepared from N$^6$-t-butoxycarbonyl-L-lysyl-L-proline t-butyl ester and the appropriate dialkyl bromomalonate by similar processes to those described in Examples 31 and 35 respectively.

EXAMPLE 38

The process described in the last part of Example 24 was repeated using certain of the diacids described in Example 33, 35 or 37 as starting materials. There were thus obtained as oils the following dimethyl esters:

$$R^1COCH_2CH_2\overset{\overset{\displaystyle COOCH_3}{|}}{C}HNHCHR^4CON\diagdown\!\!\diagup$$
$$COOCH_3$$

| R$^1$ | R$^4$ |
|---|---|
| 2-thienyl | methyl |
| 3-indolyl | methyl |
| 3-pyridyl | methyl |
| benzo[b]fur-2-yl | methyl (isolated as hydrochloride) |
| 4-biphenylyl | methyl |
| benzo[b]thien-3-yl | methyl |
| 2-thienyl | 4-aminobutyl (isolated as dihydrochloride) |
| benzo[b]fur-2-yl | 4-aminobutyl (isolated as di-trifluoroacetate) |

EXAMPLE 39

The process described in Example 12 was repeated using L-glutamyl-L-proline di-t-butyl ester and t-butyl 4-(3-indolyl)-4-oxobut-trans-2-enoate as starting materials. There were thus successively obtained N-[3-(3-indolyl)-3-oxo-1-t-butoxycarbonylpropyl]-L-glutamyl-L-proline di-t-butyl ester; and N-[1-carboxy-3-(3-indolyl)-3-oxopropyl]-L-glutamyl-L-proline trifluoroacetate.

The process described in Example 21 was repeated using the above trifluoroacetate as starting material. There was thus obtained N-[3-(3-indolyl-1-methoxycarbonyl-3-oxopropyl]-L-glutamyl-L-proline diethyl ester, which was isolated as the hydrochloride.

What we claim is:
1. An amide derivative of the formula;

$$R^1-X-A^2-\underset{\underset{\displaystyle COR^{20}}{|}}{C}H-NHCHR^4-CONR^5-CHR^6-COR^{10}$$

wherein R$^1$ is thienyl, furyl, pyrrolyl, pyridyl, benzothienyl, benzofuryl or indolyl which is unsubstituted or which bears one or two halogen or alkyl substituents, wherein X has the formula —CO— or

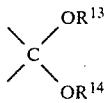

wherein $R^{13}$ and $R^{14}$, which may be the same or different, each is alkyl of up to 5 carbon atoms, or $R^{13}$ and $R^{14}$ are joined together to form alkylene of 2 to 5 carbon atoms, wherein $A^2$ is alkylene of up to 5 carbon atoms, wherein $R^4$ is hydrogen or alkyl of up to 5 carbon atoms which is unsubstituted or which bears an amino, alkoxycarbonylamino, carboxy or alkoxycarbonyl substituent each of up to 5 carbon atoms, wherein $R^5$ is hydrogen or alkyl and $R^6$ is hydrogen or alkyl of up to 5 carbon atoms which is unsubstituted or which bears an indolyl substituent, or $R^5$ and $R^6$ together form alkylene or thiaalkylene of 3 or 4 carbon atoms, and wherein $R^{10}$ and $R^{20}$, which may be the same or different, each is hydrogen or alkoxy of up to 5 carbon atoms; or a salt thereof where appropriate.

2. An amide derivative as claimed in claim 1 wherein $R^1$ is thienyl, furyl, pyrrolyl, pyridyl, benzothienyl, benzofuryl or indolyl which is unsubstituted or which bears one or two halogen or alkyl substituents; X is carbonyl, ethylene-dioxymethylene or 2,2-dimethyltrimethylene-1,3-dioxymethylene; $A^2$ has the formula —(CH$_2$)$_n$— wherein n is 1, 2, 3 or 4; $R^4$ is hydrogen, methyl, isopropyl, 4-aminobutyl, 4-(t-butoxycarbonylamino)butyl, 2-carboxyethyl, 2-methoxycarbonylethyl or 2-ethoxycarbonylethyl; $R^5$ is hydrogen or isopropyl and $R^6$ is hydrogen or 3-indolylmethyl, or $R^5$ and $R^6$ together form trimethylene or 2-thiatrimethylene; and $R^{10}$ and $R^{20}$, which may be the same or different, each is hydroxy, methoxy, ethoxy, propoxy or t-butoxy.

3. An amide derivative of the formula:

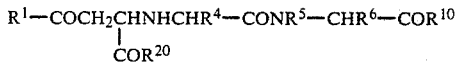

wherein $R^1$ is thienyl, furyl, pyrrolyl, pyridyl, benzothienyl, benzofuryl or indolyl which is unsubstituted or which bears one or two halogen or alkyl substituents and $R^4$, $R^5$, $R^6$, $R^{10}$ and $R^{20}$ have the meanings stated in claim 1.

4. An amide derivative as claimed in claim 3 wherein $R^1$ is 2-pyrrolyl, 1-methyl-2-pyrrolyl, 1,5-dimethyl-2-pyrrolyl, 2,5-dimethyl-3-pyrrolyl, 3-indolyl, 1-methyl-3-indolyl or 1-benzyl-3-indolyl, $R^4$ is hydrogen, methyl, isopropyl, 4-aminobutyl or 2-carboxyethyl, $R^5$ is hydrogen and $R^6$ is 3-indolylmethyl or $R^5$ and $R^6$ together form trimethylene or 2-thiatrimethylene, and $R^{10}$ and $R^{20}$, which may be the same or different, each is hydroxy or alkoxy of up to 5 carbon atoms.

5. An amide derivative as claimed in claim 4 wherein the group

is L-alanyl-L-proline, L-lysyl-L-proline, L-glutamyl-L-proline, L-valyl-L-tryptophan or N-(L-alanyl)-thiazolidine-(R)-4-carboxylic acid or a monoalkyl ester thereof, or a dialkyl ester of the glutamyl-proline, or a salt thereof.

6. An amide derivative of the formula:

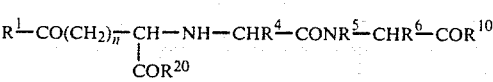

wherein $R^1$ is thienyl, furyl, pyrrolyl, pyridyl, benzothienyl, benzofuryl or indolyl which is unsubstituted or which bears one or two halogen or alkyl substituents n is 2, 3 or 4 and $R^4$, $R^5$, $R^6$, $R^{10}$ and $R^{20}$ have the meanings stated in claim 1.

7. An amide derivative as claimed in claim 6 wherein $R^1$ is thienyl, furyl, pyrrolyl, pyridyl, benzothienyl, benzofuryl or indolyl which may be unsubstituted or which may bear a chloro or methyl substituent, and wherein $R^4$, $R^5$, $R^6$, $R^{10}$ and $R^{20}$ have the meanings stated in claim 4.

8. An amide derivative as claimed in claim 7 wherein $R^1$ is one of the heterocyclic groups defined in claim 7, n is 3 and the group

is L-alanyl-L-proline, L-lysyl-L-proline, L-glutamyl-L-proline, L-valyl-L-tryptophan or N-(L-alanyl)-thiazolidine-(R)-4-carboxylic acid or a monoalkyl ester thereof, or a dialkyl ester of the glutamyl-proline, or a salt thereof.

9. The compound N-[1-carboxy-3-(1-methylpyrrol-2-yl)-3-oxopropyl]-L-alanyl-L-proline or the diethyl ester thereof;
N-[1-ethoxycarbonyl-3-oxo-3-(pyrrol-2-yl)propyl]-L-alanyl-L-proline ethyl ester;
N-[3-(2,5-dimethylpyrrol-3-yl)-1-ethoxycarbonyl-3-oxopropyl]-L-alanyl-L-proline ethyl ester;
N-[3-(1,5-dimethylpyrrol-2-yl)-1-ethoxycarbonyl-3-oxopropyl]-L-alanyl-L-proline ethyl ester;
N-[1-carboxy-3-(3-indolyl)-3-oxopropyl]-L-alanyl-L-proline or the diethyl ester thereof;
$N^1$-[1-carboxy-3-(1-methylpyrrol-2-yl)-3-oxopropyl]-L-lysyl-L-proline;
$N^1$-[1-carboxy-3-(3-indolyl)-3-oxopropyl]-L-lysyl-L-proline;
N-[1-carboxy-5-oxo-5-(2-thienyl)pentyl]-L-alanyl-L-proline or the dimethyl ester thereof or the diethyl ester thereof;
N-[1-ethoxycarbonyl-5-oxo-5-(3-thienyl)pentyl]-L-alanyl-L-proline ethyl ester;
N-[1-ethoxycarbonyl-5-(2-furyl)-5-oxopentyl]-L-alanyl-L-proline ethyl ester; or
$N^1$-[1-carboxy-5-oxo-5-(2-thienyl)pentyl]-L-lysyl-L-proline;
or a salt thereof where appropriate.

10. The compound N-[1-ethoxycarbonyl-3-1(1-methylpyrrol-2-yl)-3-oxopropyl]-L-alanyl-L-proline ethyl ester.

11. A pharmaceutical composition comprising as active ingredient an antihypertensive-effective amount of at least one amide derivative or salt thereof, claimed in claim 1, in association with a pharmaceutically-acceptable diluent or carrier therefor.

12. A composition as claimed in claim 11 which contains, in addition to the amide derivative, an effective amount of one or more drugs selected from diuretics and β-adrenergic blocking agents.

13. A method for the treatment of hypertension in a warm-blooded animal in need of such treatment which comprises administering to said animal an effective amount of an amide derivative or salt thereof claimed in claim 1.

* * * * *